Figure 1:
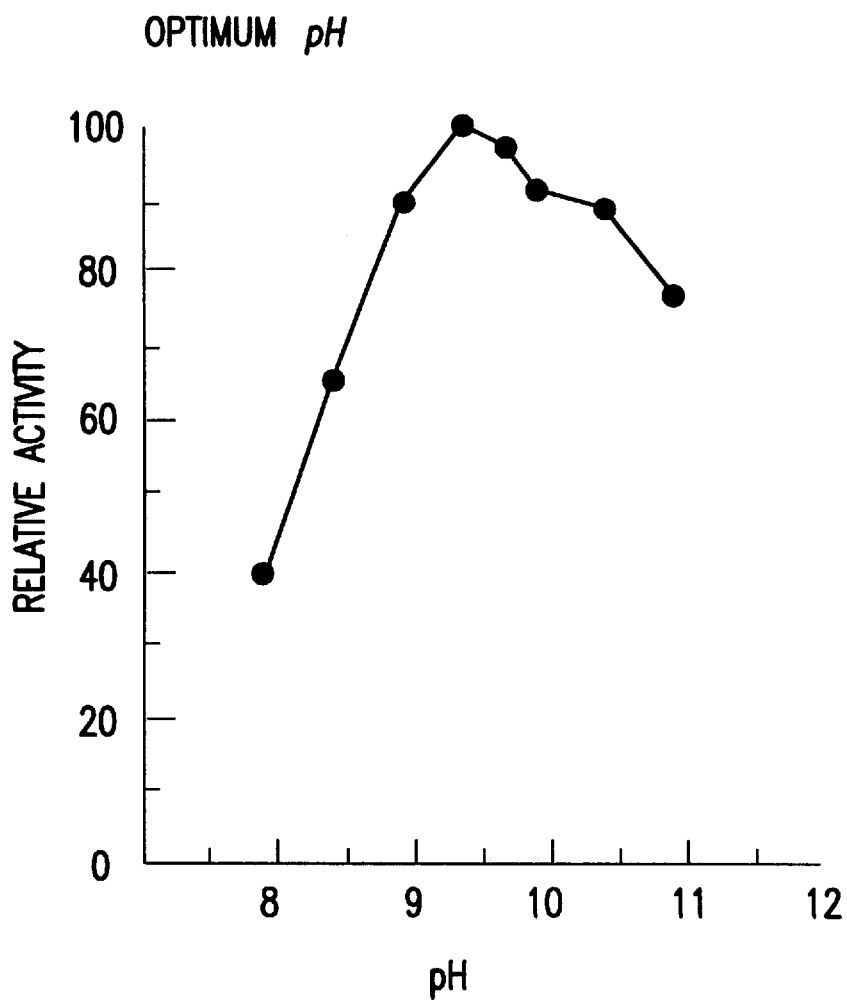

United States Patent [19]
Hattori et al.

[11] Patent Number: 5,821,061
[45] Date of Patent: Oct. 13, 1998

[54] METHOD AND REAGENT FOR DETECTING A LIGAND IN A SAMPLE

[75] Inventors: Shizuo Hattori; Kazumi Yamamoto; Shinichi Teshima; Yoshihisa Kawamura, all of Tsuruga, Japan

[73] Assignee: Toyo Boseki Kabushiki Kaisha, Osaka, Japan

[21] Appl. No.: 709,434

[22] Filed: Sep. 6, 1996

Related U.S. Application Data

[62] Division of Ser. No. 585,857, Jan. 16, 1996.

[30] Foreign Application Priority Data

Jan. 12, 1995 [JP] Japan .................................. 7-003353
Jul. 3, 1995 [JP] Japan .................................. 7-167554

[51] Int. Cl.$^6$ .............................. C12Q 1/68; C12P 19/34; C07H 19/00; C07K 1/00
[52] U.S. Cl. ........................ 435/6; 435/91.1; 435/91.2; 435/21; 435/183; 536/22.1; 536/25.32; 530/350
[58] Field of Search ............................ 435/6, 91.1, 91.2, 435/183, 196, 21; 536/22.1, 25.32; 530/350

[56] References Cited

U.S. PATENT DOCUMENTS

| | | | |
|---|---|---|---|
| 4,659,666 | 4/1987 | May et al. ............................... | 435/188 |
| 4,948,882 | 8/1990 | Ruth ........................................ | 536/27 |
| 5,118,605 | 6/1992 | Urdea ...................................... | 435/6 |

FOREIGN PATENT DOCUMENTS

WO-A-9401531  1/1994  European Pat. Off. .

OTHER PUBLICATIONS

Boyer, P.D., ed. *The Enzymes*, 3rd Edition, "Mammalian Alkaline Phosphatases" (1971) vol. 4, 417–447.

F.M. Hulett–Cowling and Campbell, L.L., Purification and Properties of an Alkaline Phosphatase of *Bacillus licheniformis* (1971) Biochemistry, vol. 10, No. 8, 1364–1371.

M. Nomoto, Ohsawa, M., Wang, H.L., Chen, C.C. and Yeh, K.W., Purification and Characterization of Extracellular Alkaline Phosphatase From an Alkalophilic Bacterium (1988) Agric. Biol. Chem., 52(7), 1643–1647.

F.M. Hulett, Stuckmann, K., Spencer, D.B., Sanopoulou, T., Purification and Characterization of the Secreted Alkaline Phosphatase of *Bacillus licheniformis* MC14: Identification of a Possible Precursor (1986) Journal of General Microbiology 132, 2387–2395.

Leary et al. "Rapid and sensitive colorimetric method for visualizing biotin–labeled probes hybridized to DNA or RNA immobilized on nitrocellulose:Bio–blots" Proc. Natl. Acad. USA, vol. 80, pp. 4045–4049, Jul. 1983.

Jablonski et al. "Preparation of oligodeoxynucleotide–alkaline phosphatase conjugates and their use as hybridization probes" Nucleic Acids Research, vol. 14, No: 15, pp. 6115–6128, 1986.

(Nomoto et al.) Agricultural and Biological Chemistry, vol. 52, No. 7, Jul., 1988, pp. 1643–1647, XP002022417, "Purification and Characterization of Extracellular Alkaline Phosphatase from an Alkalophilic Bacterium".

*Primary Examiner*—Ardin H. Marschel
*Assistant Examiner*—Jezia Riley
*Attorney, Agent, or Firm*—Kenyon & Kenyon

[57] ABSTRACT

A novel alkaline phosphatase and a method for the production of the alkaline phosphatase are described. A method for detecting a ligand in a sample and a method for analyzing the sequence of nucleic acid in a sample using the alkaline phosphatase are also described.

19 Claims, 12 Drawing Sheets

METHOD AND REAGENT FOR DETECTING A LIGAND IN A SAMPLE

This application is a division of application Ser. No. 08/585,857, filed on Jan. 16, 1996.

The present invention relates to novel alkaline phosphatase which exhibits high purity and good stability, to a method of manufacturing the same and to a method of detecting a ligand in a sample using said enzyme as a marker as well as a reagent used therefor.

Many methods have been known for detecting the biological substances and, an analytical method utilizing a biochemical affinity has been used to measure specifically a small amount of component in various substances which are present in a mixed state. For example, with regard to a component such as glucose, uric acid and the like existing in a concentration of $10^{-2}$ mole/liter or more in body fluid, a detecting method utilizing an enzymatic reaction in which said component is a substrate is frequently used, while, with regard to a component having higher molecular weight which cannot be used as a substrate or that having lower concentration, it is common to utilize ligand-receptor reaction such as antigen-antibody, hormone-receptor and nucleic acid-nucleic acid, which exhibit higher affinity for each component.

In such a detecting method, it is in many cases necessary that one of the affinity components, ligand or receptor is labeled for the detection. As one of such detecting methods, a method with a radioactive substance or radioisotope (RI) is excellent in terms of detection sensitivity and has been used already. However, it requires equipments and measuring devices by which specific radioisotopes are handled. Accordingly, a method with an enzyme as a marker has been used in recent years. In the method, one of the affinity components is labeled with an enzyme, and the enzymatic activity of the marker which is bonded as a result of ligand-receptor reaction or is not bonded is measured whereby another affinity component is quantitatively determined.

A significant improvement in the detection sensitivity has been attempted for changing the substrate used for detecting the labeled enzyme from a substrate for colorimetric method to that for fluorescent method or, furthermore, that for chemiluminescence method.

Examples of the conditions or requirements for labeled enzyme are that, in general, purity is high, stability is high, turnover is high, functional group which is apt to be labeled is contained, Km value to the substrate is low, background is low and the substrate which is suitable for the detection is available. Examples of the applicable enzyme are alkaline phosphatase. β-galactosidase, glucose oxidase, glucose-6-phosphate dehydrogenase, peroxidase, β-lactamase, glucoamylase and lysozyme and a big advantage of alkaline phosphatase among the above enzymes is that its background is lower than those of other enzymes and that the substrates suitable for detection are available.

With regard to the substrates for alkaline phosphatase which are suitable for detecting antigen, antibody or nucleic acid, p-nitrophenyl phosphate, 5-bromo-4-chloro-3-indolyl phosphate, 4-methylumbelliferone phosphate and chemiluminescent dioxetanes (PPD, AMPPD, etc.) have been used already. When visible light, fluorescence or luminescence resulted by the reaction of those substrates with alkaline phosphatase is measured, the amount of the biological substance can be determined.

With regard to the alkaline phosphatase which exhibits the above-mentioned properties to the highest extent, that which is derived from calf intestine may be exemplified and has been used most commonly.

The alkaline phosphatase derived from calf intestine has a specific activity of not less than 3,000 U/mg and has a sugar chain and, therefore, it can be labeled by a periodic acid method whereby it is said to be better than the enzymes derived from others. On the other hand, however, said alkaline phosphatase has been known to exhibit little stability and, due to the sugar chain therein, a background is generated (Besman, M., Coleman, J. E., J. Biol. Chem. 260, 1190(1985); Japanese Laid-Open Patent Publication Sho-60/180584).

In addition, alkaline phosphatase derived from *Escherichia coli* shows a good stability and its sample having a high purity is easily available but, its specific activity is as low as 60 U/mg and is not suitable for use as an enzyme for labeling whereby it has been used only as an enzyme for dephosphorylation in molecular biology (Reid, R. W., Wilson, I. B. in "The Enzymes", 3rd Edition, 373 (1971)).

For improving those enzymes, there has been an attempt in which the amino acids in alkaline phosphatase derived from *E. coli* are substituted by means of a site-specific mutation (Japanese Laid-Open Patent Publication Hei-4/349881). However, the mutant alkaline phosphatase obtained there shows an only increase in 3.9 times as much in the specific activity and is not comparable with that derived from calf intestine.

There have been other attempts for obtaining alkaline phosphatase having a high specific activity from nature and the papers on the enzyme derived from alkalophilic Bacillus species (Nomoto, M., et al., Agric. Biol. Chem., 52(7), 1643 (1988)) and that derived from *Bacillus licheniformis* (Hulett, F. M., J. Gen. Microbiol., 132, 2387 (1986)) have been reported.

However, specific activity of the former is 1,650 U/mg and can be hardly said that it is as good as that derived from calf intestine. In the latter, its specific activity is 2115.9 U/mg but the measurement of the enzymatic activity is conducted at 55° C. and there is a paper reporting that the activity at the practical temperature of 37° C. is expected to be not more than 70% thereof (Hulett, F. M., et al., Biochemistry, 10(8), 1364 (1971)).

There has been a demand for obtaining an alkaline phosphatase from microorganisms which exhibits a higher purity, a higher stability and a specific activity which is nearly as same as that of the enzyme derived from calf intestine.

The present inventors have conducted an extensive study for solving the above-mentioned problems and have found an alkaline phosphatase having an excellent stability against heat and a high specific activity from microorganisms beloging the genus Bacillus whereupon the present invention has been achieved.

Thus, the present invention relates to an alkaline phosphatase having the following physical and chemical properties.

1. It catalyzes the following reaction:

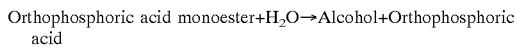
   Orthophosphoric acid monoester+$H_2O$→Alcohol+Orthophosphoric acid 2. Activators and stabilizers: $Mg^{++}$ and $Co^{++}$.
3. Thermal stability: Stable at least for 30 minutes when treated at pH 7.5 and at 60° C.
4. Specific activity: at least 2,300 U/mg.
5. It has no sugar chain.
6. Molecular weight: 140,000–150,000 (gel filtration) 65,000–67,000 (SDS-PAGE)

The term of "stable" in thermal stability is defined that residual activity is not less than 80%.

One specific example of the present invention is an alkaline phosphatase having the following physical and chemical properties:

1. It catalyzes the following reaction:

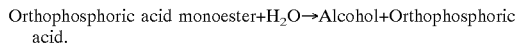
Orthophosphoric acid monoester+$H_2O$→Alcohol+Orthophosphoric acid.

2. Activators and stabilizers: $Mg^{++}$ and $Co^{++}$.
3. Thermal stability: not higher than 60° C. (at pH 7.5 for 30 minutes).
4. Optimum temperature: not lower than 60° C.
5. Stable pH: pH 6–9 (at 25° C. for 16 hours).
6. Optimum pH: pH 9–10.
7. Specific activity: at least 2,300 U/mg.
8. It has no sugar chain.
9. Km value: 0.34 mM (to p-nitrophenylphosphoric acid).
10. Molecular weight: 140,000–150,000 (gel filtration) 65,000–67,000 (SDS-PAGE)
11. Substrate specificity: It acts on p-nitrophenyl phosphate, 4-methylumbelliferone phosphate, NADP, DL-α-glycerophosphate, β-glycerophosphate, phenylphosphate, phosphoethanolamine and glucose-6-phosphate.

Another specific example of the present invention is an alkaline phosphatase having the following physical and chemical properties.

1. It catalyzes the following reaction:

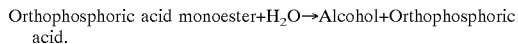
Orthophosphoric acid monoester+$H_2O$→Alcohol+Orthophosphoric acid.

2. Activators and stabilizers: $Mg^{++}$ and $Co^{++}$.
3. Thermal stability: not higher than 60° C. (at pH 7.5 for 30 minutes).
4. Optimum temperature: not lower than 60° C.
5. Stable pH: pH 6–9 (at 25° C. for 16 hours).
6. Optimum pH: pH 9–10.
7. Specific activity: at least 2,300 U/mg.
8. It has no sugar chain.
9. Km value: 0.26 mM (to p-nitrophenyl phosphoric acid).
10. Molecular weight: 140,000–150,000 (gel filtration) 65,000–67,000 (SDS-PAGE)
11. Substrate specificity: It acts on p-nitrophenyl phosphate, 4-methylumbelliferone phosphate, NADP, DL-α-glycerophosphate, β-glycerophosphate, phenylphosphate, phosphoethanolamine and glucose-6-phosphate.

Still another specific example of the present invention is an alkaline phosphatase having the following physical and chemical properties:

1. It catalyzes the following reaction:

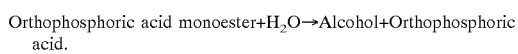
Orthophosphoric acid monoester+$H_2O$→Alcohol+Orthophosphoric acid.

2. Activators and stabilizers: $Mg^{++}$ and $Co^{++}$.
3. Thermal stability: not higher than 70° C. (at pH 7.5 for 30 minutes).
4. Optimum temperature: not lower than 60° C.
5. Stable pH: pH 6–11 (at 25° C. for 16 hours).
6. Optimum pH: pH 9.5–10.
7. Specific activity: at least 2,300 U/mg.
8. It has no sugar chain.
9. Km value: 0.28 mM (to p-nitrophenyl phosphoric acid).
10. Molecular weight: 140,000–150,000 (gel filtration) 65,000–67,000 (SDS-PAGE)
11. Substrate specificity: It acts on p-nitrophenyl phosphate, 4-methylumbelliferone phosphate, NADP, DL-α-glycerophosphate, β-glycerophosphate, phenylphosphate, phosphoethanolamine, glucose-1-phosphate and glucose-6-phosphate.

The present invention also relates to a method of manufacturing an alkaline phosphatase, characterized in that, a strain which belongs to the genus Bacillus and has an ability of producing the alkaline phosphatase having the above-mentioned physical and chemical properties is cultured in a medium and the alkaline phosphotase is collected from the cultured product.

The present invention also relates to a method of detecting a ligand in a sample, characterized in that, an alkaline phosphatase having the following physical and chemical properties as a marker.

1. It catalyzes the following reaction:

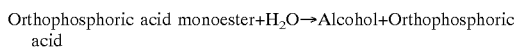
Orthophosphoric acid monoester+$H_2O$→Alcohol+Orthophosphoric acid

2. Activators and stabilizers: $Mg^{++}$ and $Co^{++}$.
3. Thermal stability: It is stable at least for 30 minutes when treated at pH 7.5 and 60° C.
4. Specific activity: at least 2,300 U/mg.
5. It has not sugar chain.
6. Molecular weight: 140,000–150,000 (gel filtration) 65,000–67,000 (SDS-PAGE)

The present invention also relates to a reagent for detecting a ligand in a biological sample containing (i) a substance which specifically reacts with a ligand labeled with an alkaline phosphatase having the following physical and chemical properties or (ii) a ligand which is labeled with an alkaline phosphatase having the following physical and chemical properties and a substance which specifically reacts with a ligand and (iii) a reagent for measuring an alkaline phosphatase.

1. It catalyzes the following reaction:

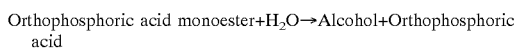
Orthophosphoric acid monoester+$H_2O$→Alcohol+Orthophosphoric acid

2. Activators and stabilizers: $Mg^{++}$ and $Co^{++}$.
3. Thermal stability: It is stable at least for 30 minutes when treated at pH 7.5 and 60° C.
4. Specific activity: at least 2,300 U/mg.
5. It has not sugar chain.
6. Molecular weight: 140,000–150,000 (gel filtration) 65,000–67,000 (SDS-PAGE).

The present invention further relates to a reagent for detecting a ligand in a biological sample containing (i) a substance having a specific affinity for a ligand to which avidin or biotin is bonded, (ii) an alkaline phosphatase having the following physical and chemical properties to which biotin or avidin is bonded and (iii) a substance which measures an alkaline phosphatase.

1. It catalyzes the following reaction:

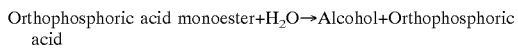
Orthophosphoric acid monoester+$H_2O$→Alcohol+Orthophosphoric acid

2. Activators and stabilizers: $Mg^{++}$ and $Co^{++}$.
3. Thermal stability: It is stable at least for 30 minutes when treated at pH 7.5 and 60° C.
4. Specific activity: at least 2,300 U/mg.
5. It has no sugar chain.
6. Molecular weight: 140,000–150,000 (gel filtration) 65,000–67,000 (SDS-PAGE).

The present invention also relates to a method of quantitative determination of a ligand in a biological sample, characterized in that, an alkaline phosphatase having the following physical and chemical properties is used as a marker.

1. It catalyzes the following reaction:

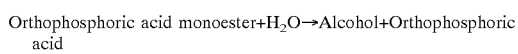
Orthophosphoric acid monoester+$H_2O$→Alcohol+Orthophosphoric acid

2. Activators and stabilizers: $Mg^{++}$ and $Co^{++}$.
3. Thermal stability: It is stable at least for 30 minutes when treated at pH 7.5 and 60° C.
4. Specific activity: at least 2,300 U/mg.
5. It has no sugar chain.
6. Molecular weight: 140,000–150,000 (gel filtration) 65,000–67,000 (SDS-PAGE).

The present invention also relates to a method of analysing the sequence of nucleic acid in a sample, characterized in that, an alkaline phosphatase having the following physical and chemical properties as a marker.

1. It catalyzes the following reaction:

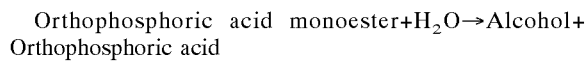
Orthophosphoric acid monoester+$H_2O$→Alcohol+ Orthophosphoric acid

2. Activators and stabilizers: $Mg^{++}$ and $Co^{++}$.
3. Thermal stability: It is stable at least for 30 minutes when treated at pH 7.5 and 60° C.
4. Specific activity: at least 2,300 U/mg.
5. It has no sugar chain.
6. Molecular weight: 140,000–150,000 (gel filtration) 65,000–67,000 (SDS-PAGE).

With regard to a source of the enzyme of the present invention, any source such as animals, plants and microorganisms may be used so far as it is capable of producing the alkaline phosphatase having the above-mentioned physical and chemical properties. Preferred ones are the bacteria of the genus Bacillus capable of producing the alkaline phosphatase having the above-mentioned properties and suitable examples are *Bacillus badius* TE3592 (FERM BP-5329), *Bacillus badius* TE3593 (FERM BP-5330) and *Bacillus badius* TE3597 (FERM BP-5120). Incidentally, *Bacillus badius* TE3592 and *Bacillus badius* TE3593 are the strains isolated from the soil collected at Yogo-cho, Ika-ku, Shiga Prefecture while *Bacillus badius* TE3597 is the strain isolated from the soil collected at Takefu-shi, Fukui Prefecture and their mycological properties are as follows.

(A) *Bacillus badius* TE3592
(a) Morphology
(1) Shape: short bacillus
(2) Size of cells: 0.6×1.8–3.0 μm
(3) Polymorphism of cells: none
(4) Motility: none
(5) Spores: Endospores were elliptic and observed at the center or terminals of the cells. Swelling of the endospores was not observed.

(b) State of growth on a medium.
(1) Bouillon agar plate medium: Light greyish yellow colonies were formed when cultured at 30° C. for 24 hours. Circumferences of the colonies were erose and convex. Surfaces were smooth having a luster and were transluscent.
(2) Bouillon liquid culture: Growth was normal and homogeneously turbid. Neither semimentation nor fairy ring was formed.
(3) Bouillon gelatin stab culture: Growth was normal and only upper parts grew in a filiform. Liquefaction of gelatin was weak.
(4) Litmus milk: No change in color. Milk was not solidified.
(5) MacConkey's agar medium: no growth.
(6) Phenylethyl alcohol agar medium: grew but poor.
(c) Physiological Properties.
(1) Gram stain: negative (−) or indefinite
(2) Reduction of nitrate: −
(3) Denitrification: −
(4) MR test: −
(5) VP test: −
(6) Production of indole: −
(7) Production of hydrogen sulfide: −
(8) Decomposition of starch: −
(9) Decomposition of casein: +
(10) Decomposition of gelatin: +
(11) Decomposition of tyrosine: +
(12) Decomposition of Tween 80: −
(13) Utilization of citric acid:
    Koser's medium: −
    Christensen's medium: −
(14) Utilization of inorganic nitrogen sources (carbon source was dl-malic acid):
    Sodium nitrate: −
    Ammonium sulfate: +
    Sodium glutamate: +
(15) Formation of dyes: −
(16) Urease: −
(17) Oxidase: +
(18) Catalase: +
(19) β-Glactosidase: −
(20) Arginine dihydrase: −
(21) Lysine carboxylase: −
(22) Ornithine carboxylase: −
(23) Tryptophane deaminase: −
(24) β-Glucosidase: −
(25) Exocellular DNase: −
(26) Ranges for growth:

| Growth temperature: | |
|---|---|
| 10° C. | − |
| 20° C. | + |
| 25° C. | + |
| 30° C. | + |
| 37° C. | + |
| 40° C. | + |
| 50° C. | − |

-continued

| Growth pH | |
|---|---|
| pH 4 | − |
| pH 7 | + |
| pH 9 | + |
| NaCl concentration | |
| 2% | + |
| 5% | + |

(27) Behavior to oxygen: aerophilic
(28) O-F Test (Hugh Leifson method): − (sugar was not decomposed)
(29) Production of acid and gas from sugars:

|  | Acid | Gas |
|---|---|---|
| L-Arabinose | − | − |
| D-Xylose | − | − |
| D-Glucose | − | − |
| D-Mannose | − | − |
| D-Fructose | − | − |
| D-Galactose | − | − |
| Maltose | − | − |
| Sucrose | − | − |
| Lactose | − | − |
| Trehalose | − | − |
| D-Sorbitol | − | − |
| D-Mannitol | − | − |
| Inositol | − | − |
| Glycerol | − | − |
| Starch | − | − |
| L-Rhamnose | − | − |
| D-Melibiose | − | − |
| D-Amygdalin | − | − |

(30) Utilization of organic compounds.

| | |
|---|---|
| D-Glucose | − |
| L-Arabinose | − |
| D-Mannose | − |
| D-Mannitol | − |
| N-Acetyl-D-glucosamine | − |
| Maltose | − |
| Potassium gluconate | + |
| n-Capric acid | − |
| Adipic acid | − |
| dl-Malic acid | + |
| Phenyl acetate | − |

(B) *Bacillus badius* TE3593.
(a) Morphology
(1) Shape: short bacillus
(2) Size of cells: 0.4×1.3–2.8 μm
(3) Polymorphism of cells: none
(4) Motility: none
(5) Spores: Endospores were elliptic and observed at the center or terminals of the cells. Swelling of the endospores was not observed.
(b) State of growth on a medium.
(1) Bouillon agar plate medium: Light greyish yellow colonies were formed when cultured at 30° C. for 24 hours. Circumferences of the colonies were erose and convex. Surfaces were smooth having a luster and were translucent.
(2) Bouillon liquid culture: Growth was normal and homogeneously turbid. Neither semimentation nor fairy ring was formed.
(3) Bouillon gelatin stab culture: Growth was normal and only upper parts grew in a filiform. Liquefaction of gelatin was weak.
(4) Litmus milk: No change in color. Milk was not solidified.
(5) MacConkey's agar medium: no growth.
(6) Phenylethyl alcohol agar medium: grew but poor.
(c) Physiological Properties.
(1) Gram stain: negative (−) or indefinite
(2) Reduction of nitrate: −
(3) Denitrification: −
(4) MR test: −
(5) VP test: −
(6) Production of indole: −
(7) Production of hydrogen sulfide: −
(8) Decomposition of starch: −
(9) Decomposition of casein: +
(10) Decomposition of gelatin: +
(11) Decomposition of tyrosine: +
(12) Decomposition of Tween 80: −
(13) Utilization of citric acid:
    Koser's medium: −
    Christensen's medium: −
(14) Utilization of inorganic nitrogen sources (carbon source was dl-malic acid):
    Sodium nitrate: −
    Ammonium sulfate: +
    Sodium glutamate: +
(15) Production of dyes: −
(16) Urease: −
(17) Oxidase: +
(18) Catalase: +
(19) β-Glactosidase: −
(20) Arginine dihydrase: −
(21) Lysine carboxylase: −
(22) Ornithine carboxylase: −
(23) Tryptophane deaminase: −
(24) β-Glucosidase: −
(25) Exocellular DNase: −
(26) Ranges for growth:

| Growth temperature: | |
|---|---|
| 10° C. | − |
| 20° C. | + |
| 25° C. | + |
| 30° C. | + |
| 37° C. | + |
| 40° C. | + |
| 50° C. | − |
| Growth pH | |
| pH 4 | − |
| pH 7 | + |
| pH 9 | + |
| NaCl concentration | |
| 2% | + |
| 5% | + |

(27) Behavior to oxygen: aerophilic
(28) O-F Test (Hugh Leifson method): − (sugar was not decomposed)

(29) Production of acid and gas from sugars:

|  | Acid | Gas |
|---|---|---|
| L-Arabinose | − | − |
| D-Xylose | − | − |
| D-Glucose | − | − |
| D-Mannose | − | − |
| D-Fructose | − | − |
| D-Galactose | − | − |
| Maltose | − | − |
| Sucrose | − | − |
| Lactose | − | − |
| Trehalose | − | − |
| D-Sorbitol | − | − |
| D-Mannitol | − | − |
| Inositol | − | − |
| Glycerol | − | − |
| Starch | − | − |
| L-Rhamnose | − | − |
| D-Melibiose | − | − |
| D-Amygdalin | − | − |

(30) Utilization of organic compounds.

| D-Glucose | − |
|---|---|
| L-Arabinose | − |
| D-Mannose | − |
| D-Mannitol | − |
| N-Acetyl-D-glucosamine | − |
| Maltose | − |
| Potassium gluconate | + |
| n-Capric acid | − |
| Adipic acid | − |
| dl-Malic acid | + |
| Citric acid | − |
| Phenyl acetate | − |

(C) Bacillus badius TE3597.
(a) Morphology
(1) Shape: short bacillus
(2) Size of cells: 1.0×3.3–4.0 μm
(3) Polymorphism of cells: none
(4) Motility: none
(5) Spores: Endospores were elliptic and observed at the center or terminals of the cells. Swelling of the endospores was not observed.
(b) State of growth on a medium.
(1) Bouillon agar plate medium: Light greyish yellow colonies were formed when cultured at 30° C. for 24 hours. Circumferences of the colonies were erose and convex. Surfaces were smooth having a luster and were transluscent.
(2) Bouillon liquid culture: Growth was normal and homogeneously turbid. Neither semimentation nor fairy ring was formed.
(3) Bouillon gelatin stab culture: Growth was normal and only upper parts grew in a filiform. Liquefaction of gelatin was weak.
(4) Litmus milk: No change in color. Milk was not solidified.
(5) MacConkey's agar medium: no growth.
(6) Phenylethyl alcohol agar medium: grew but poor.
(c) Physiological Properties.
(1) Gram stain: positive (+)
(2) Reduction of nitrate: negative (−)
(3) Denitrification: −
(4) MR test: −
(5) VP test: −
(6) Production of indole: −
(7) Production of hydrogen sulfide: −
(8) Decomposition of starch: −
(9) Decomposition of casein: +
(10) Decomposition of gelatin: +
(11) Decomposition of tyrosine: +
(12) Decomposition of Tween 80: −
(13) Utilization of citric acid:
    Koser's medium: −
    Christensen's medium: −
(14) Utilization of inorganic nitrogen sources (carbon source was dl-malic acid):
    Sodium nitrate: −
    Ammonium sulfate: +
    Sodium glutamate: +
(15) Production of dyes: −
(16) Urease: −
(17) Oxidase: +
(18) Catalase: +
(19) β-Glactosidase: −
(20) Arginine dihydrase: −
(21) Lysine carboxylase: −
(22) Ornithine carboxylase: −
(23) Tryptophane deaminase: −
(24) β-Glucosidase: −
(25) Exocellular DNase: −
(26) Ranges for growth:

| Growth temperature: | |
|---|---|
| 10° C. | − |
| 20° C. | + |
| 25° C. | + |
| 30° C. | + |
| 37° C. | + |
| 40° C. | + |
| 50° C. | − |
| Growth pH | |
| pH 4 | − |
| pH 7 | + |
| pH 9 | + |
| NaCl concentration | |
| 2% | + |
| 5% | + |

(27) Behavior to oxygen: aerophilic
(28) O-F Test (Hugh Leifson method): − (sugar was not decomposed)
(29) Production of acid and gas from sugars:

|  | Acid | Gas |
|---|---|---|
| L-Arabinose | − | − |
| D-Xylose | − | − |
| D-Glucose | − | − |
| D-Mannose | − | − |
| D-Fructose | − | − |
| D-Galactose | − | − |
| Maltose | − | − |
| Sucrose | − | − |
| Lactose | − | − |
| Trehalose | − | − |

-continued

|  | Acid | Gas |
|---|---|---|
| D-Sorbitol | − | − |
| D-Mannitol | − | − |
| Inositol | − | − |
| Glycerol | − | − |
| Starch | − | − |
| L-Rhamnose | − | − |
| D-Melibiose | − | − |
| D-Amygdalin | − | − |

(30) Utilization of organic compounds.

| D-Glucose | − |
|---|---|
| L-Arabinose | − |
| D-Mannose | − |
| D-Mannitol | − |
| N-Acetyl-D-glucosamine | + |
| Maltose | − |
| Potassium gluconate | − |
| n-Capric acid | − |
| Adipic acid | − |
| dl-Malic acid | + |
| Citric acid | − |
| Phenyl acetate | + |

Method of experiment for identifying the above-mentioned mycological properties was carried out mostly in accordance with "Classification and Identification of Microorganisms" (Revised Edition) edited by Takeji Hasegawa (Gakkai Shuppan Center; 1985). As a standard for classification and identification, "Bergey's Manual of Systematic Bacteriology" (1984) was referred to.

When the above-mentioned literature and mycological properties are referred to, it is believed that they belong to the genus Bacillus because, though there is a difference in terms of production of exocellular DNase, all of them are aerophilic bacilli which are unstable to Gram stain and are capable of producing the spores. When the facts that endospores are elliptic and do not sweel, no acid is producted from D-glucose and, though geletin is decomposed, starch is not decomposed are taken into consideration, it is belived that all of them belong to *Bacillus badius* in the genus Bacillus and they were named as *Bacillus badius* TE3592, *Bacillus badius* TE 3593 and *Bacillus badius* TE3597, respectively.

Remarks:

(1) Bacillus badius TE3597 has been deposited on Jun. 1, 1995 under the Budapest Treaty under the Deposit No. FERM BP-5120 while *Bacillus badius* TE3592 and *Bacillus badius* TE3593 have been deposited on Dec. 2, 1994 (domestic deposit) under Deposit Nos. FERM P-14683 and FERM P-14684, respectively, and have been converted into international deposit on Dec. 7, 1995 under Deposit Nos. FERM BP-5329 and FERM BP-5330, respectively. In all cases, the International Depositary Authority is National Institute of Science and Human-Technology, Agency of Industrial Science and Technology, of 1–3, Higashi 1-chome, Tsukuba-shi, Ibaraki-ken 305, Japan.

In the manufacture of the enzyme of the present invention, the above-mentioned microorganims capable of producing alkaline phosphatase is cultured in a nutrient medium and the alkaline phosphatase is collected from said cultured medium. With regard to a medium used for the culture of the alkaline phosphatase-productive microorganisms, any of synthetic and natural media may be used so far as it contains suitable amounts of carbon sources, nitrogen sources, inorganic substances and other nutrients which can be utilized by the strain used. Examples of the carbon sources applicable are glucose and glycerol. Examples of the nitrogen sources applicable are nitrogen-containing natural substances such as peptones, meat extract and yeast extract and inorganic nitrogen-containing compounds such as ammonium chloride and ammonium citrate. Examples of the inorganic substances applicable are potassium phosphate, sodium phosphate and magnesium sulfate. Incidentally, it is desirable that the concentration of phosphoric acid is made low for inducing the production of alkaline phosphatase.

Culturing is usually conducted by a shake culture or by a culture with aeration and stirring. It is recommend to control the culturing temperature to 20°–40° C. or, preferably, 25°–37° C. and the culturing pH to 5–11 or, preferably, 6–10. The conditions outside of the above range may be conducted as well provided that the used strain can grow. With regard to the culturing time, growth is resulted usually for 1–7 days whereupon alkaline phosphatase is produced and accumulated both inside and outside of the cells.

With regard to a method for purifying the enzyme of the present invention, that which has been commonly used may be used. For example, the medium after removal of the cells can be purified by means of a salting-out method using ammonium sulfate or sodium sulfate, a metal aggregating method using magnesium chloride or calcium chloride, an aggregating method using protamine or polyethyleneimine or an ion exchange chromatographic method using DEAE (diethylaminoethyl) cellulose or CM (carboxymethyl) Sepharose. Crude enzymatic liquid or purified enzymatic liquid obtained by those methods may also be pulverized, for example, by a spray drying or a freeze drying. Further, it may be used as an immobilized enzyme by immobilizing with a suitable carrier.

Then, a method of measuring the activity of the alkaline phosphatase of the present invention will be given as hereunder.

First, the following reaction mixture liquid is prepared in a cuvette and preliminarily warmed at 37° C. for about five minutes.

3.00 ml of 1M diethanolamine buffer (pH: 9.8) containing 0.1 mM of $CoCl_2$ and 0.5 mM of $MgCl_2$; and 0.05 ml of 0.67M p-nitrophenyl phosphate buffer Then 0.05 ml of an enzyme solution is added thereto followed by gentle mixing, changes in the absorbance at 405 nm are recorded for 3–4 minutes by a spectrophotometer controlled at 37° C. using water as a control and, from its initial linear part, changes in the absorption per minute are determined. A blind test is conducted as follows. Thus, a diluted enzyme solution (50 mM Tris hydrochloride buffer of pH 7.5 containing 0.05 mM of $CoCl_2$ and 0.05 mM of $MgCl_2$) instead of the enzyme solution is added to the reaction mixture solution, then the same operations as mentioned above are conducted and absorbance per minute is determined. Amount of the enzyme which produces one micromole of p-nitrophenol per minute under the above conditions is defined as one unit (U).

A specific method for detecting a ligand in the sample of the present invention is a method in which an affinity reaction of the ligand with a substance having a specific affinity for the ligand is utilized and the activity of the alkaline phosphatase bonded with the substance which is formed by said reaction is determined or is a method in which the activity of the alkaline phosphatase which is not bonded therewith is determined.

Examples of the ligand in the sample in the present invention are antigen, antibody, hormone, hormone receptor or nucleic acid.

Examples of the affinity reaction of ligand with a substance having a specific affinity for the ligand are antigen-antibody reaction, hormone-hormone receptor reaction and nucleic acid hybridation reaction.

With regard to the alkaline phosphatase which is used for the present invention, that of any source may be used so far as it is an alkaline phosphatase having the above-mentioned physical and chemical properties. A suitable example is an alkaline phosphatase of the genus Bacillus. Its examples are the alkaline phosphatases of *Bacillus badius* TE3592 and *Bacillus badius* TE3593 and that of *Bacillus badius* TE3597.

Physical and chemical properties of the alkaline phosphatase of *Bacillus badius* TE3592 are as follows.

1. It catalyzes the following reaction:

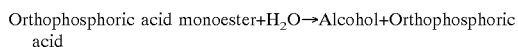
Orthophosphoric acid monoester+H$_2$O→Alcohol+Orthophosphoric acid

2. Substrate specificity: It acts on p-nitrophenyl phosphate, 4-methylumbelliferone phosphate, NADP, DL-α-glycerophosphate, β-glycerophosphate, phenylphosphate, phosphoethanolamine and glucose-6-phosphate.
3. Km value: 0.34 mM (to p-nitrophenyl phosphoric acid).
4. Optimum pH: pH 9–10.
5. Stable pH: pH 6–9 (at 25° C. for 16 hours).
6. Optimum temperature: not lower than 60° C.
7. Activators and stabilizers: Mg$^{2+}$ and Co$^{2+}$.
8. Specific activity: at least 2,300 U/mg.
9. It has no sugar chain.
10. Thermal stability: not higher than 60° C. (at pH 7.5 for 30 minutes).
11. Molecular weight: 140,000–150,000 (gel filtration) 65,000–67,000 (SDS-PAGE).

Physical and chemical properties of the alkaline phosphatase of *Bacillus badius* TE3593 are as follows.

1. It catalyzes the following reaction:

Orthophosphoric acid monoester+H$_2$O→Alcohol+Orthophosphoric acid

2. Substrate specificity: It acts on p-nitrophenyl phosphate, 4-methylumbelliferone phosphate, NADP, DL-α-glycerophosphate, β-glycerophosphate, phenylphosphate, phosphoethanolamine and glucose-6-phosphate.
3. Km value: 0.26 mM (to p-nitrophenyl phosphoric acid).
4. Optimum pH: pH 9–10.
5. Stable pH: pH 6–9 (at 25° C. for 16 hours).
6. Optimum temperature: not lower than 60° C.
7. Activators and stabilizers: Mg$^{2+}$ and Co$^{2+}$.
8. Specific activity: at least 2,300 U/mg.
9. It has no sugar chain.
10. Thermal stability: not higher than 60° C. (at pH 7.5 for 30 minutes).
11. Molecular weight: 140,000–150,000 (gel filtration) 65,000–67,000 (SDS-PAGE).

Physical and chemical properties of the alkaline phosphatase of *Bacillus badius* TE3597 are as follows.

1. It catalyzes the following reaction:

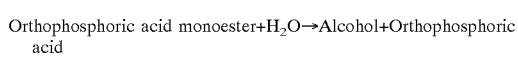
Orthophosphoric acid monoester+H$_2$O→Alcohol+Orthophosphoric acid

2. Substrate specificity: It acts on p-nitrophenyl phosphate, 4-methylumbelliferone phosphate, NADP, DL-α-glycerophosphate, β-glycerophosphate, phenylphosphate, phosphoethanolamine, glucose-1-phospohate and glucose-6-phosphate.
3. Km value: 0.28 mM (to p-nitrophenyl phosphoric acid).
4. Optimum pH: pH 9.5–10.
5. Stable pH: pH 6–11 (at 25° C. for 16 hours).
6. Optimum temperature: not lower than 60° C.
7. Activators and stabilizers: Mg$^{2+}$ and Co$^{2+}$.
8. Specific activity: at least 2,300 U/mg.
9. It has no sugar chain.
10. Thermal stability: not higher than 70° C. (at pH 7.5 for 30 minutes).
11. Molecular weight: 140,000–150,000 (gel filtration) 65,000–67,000 (SDS-PAGE).

Examples of the substance which labels the alkaline phosphatase in the present invention are antigens which are substances having a high molecular weight such as protein and nucleic acid. Peptides in which an epitope site of antigen is designed which has been much used recently may be used as well. With regard to antibody, the commonly-used ones such as polyclonal antibody obtained by immunization to goats, rabbits and guinea pigs, monoclonal antibody obtained from hybridoma of abdominal dropsy of mouse and antigen-bonded active fragment (Fab') prepared by treating those antibodies with protease may be used. It is also possible to use protein having antigen-bonding activity such as Fv antibody and single stranded Fv antibody obtained by a gene recombinant technique.

In the present invention, it is preferred that the alkaline phosphatase is bonded with any of a ligand and a substance which has a specific affinity for the ligand.

With regard to a method which is used for labeling the alkaline phosphatase with the above-mentioned antigen or antibody, glutaraldehyde method, maleimide method, carbodiimide method, pyridine disulfide method, etc. may be used and the preferred ones are maleimide method or the like in which the activity of antigen, antibody and enzyme is not lowered.

With regard to the enzyme for labeling which is to be introduced into one molecule of antibody or antigen, it is usually preferred to use an enzyme marker to which one or more molecule(s), preferably two or more molecules, is/are bonded.

One specific example of the present invention is that a ligand in the sample such as antigen or antibody is made to react with a substance bonded with an alkaline phosphatase and having a specific affinity for said ligand such as antibody or antigen, reaction products and unreacted substances are separated and the activity of the alkaline phosphatase bonded with the reaction products or the activity of the alkaline phosphatase of the unreacted substances is measured.

The immunoassay using an alkaline phosphatase as a labeled substance can be used for a competitive method or a heterogenous method of a noncompetitive method in the measurement of both antibody and antigen. In any of the methods, it is possible to label an alkaline phosphatase thereto not only in a method using primary antibody but also in a method using secondary antibody. Further, instead of the secondary antibody, Fc receptor such as protein A and protein G can be used by labeling with an alkaline phosphatase.

Another specific example of the present invention is a method of detecting a ligand in which a ligand or a substance having a specific affinity for the ligand is bonded to a solid phase. With regard to the solid phase, the conventionally known ones such as polystyrene beads may be used.

Still another specific example is a method of detecting a ligand in a sample in which avidin or biotin is bonded with a substance (e.g. antibody or antigen) having a specific affinity for a ligand while alkaline phosphatase is bonded with biotin or avidin and, simultaneously with or after an affinity reaction of a ligand with a substance (e.g. antibody or antigen) having a specific affinity for the ligand, a reaction of binding avidin with biotin is conducted and the alkaline phosphatase activity bonded by said reaction or the residual alkaline phosphatase activity is measured.

Avidin compounds are sugar proteins which can bind with biotin strongly and are exampled by avidin, streptoavidin and the like. And biotin compounds are ones of vitamine B complexes and biotin is represented.

Binding constants of avidin and biotin are as high as in a level of $10^{15}M^{-1}$, avidin has four sites for binding with biotin and introduction of biotin has little loss in the activity of, for example, antibody. Accordingly, an avidin-biotin system has a big advantage.

In a solid phase sandwich immunoassay for example, antibody which is immobilized with a solid phase is made to react with a sample, then made to react with antibody which is bonded with biotin and, after that, biotin in the reaction product or that in the unreacted substance is detected by avidin which is labeled with alkaline phosphatase. Avidin and streptoavidin which is a analogous substance thereof are proteins with a molecular weight of about 50,000 and they can be bonded with alkaline phosphatase by glutaraldehyde method, maleimide method, carbodiimide method, pyridine disulfide method, etc.

On the other hand, when an antibody bonded with avidin instead of biotin is used, a detection is conducted with biotin which is labeled with alkaline phosphatase and avidin after the antigen-antibody reaction. Reagents which biotinizes the alkaline phosphatase are available in market and their examples are biotin-N-hydroxysuccinimide ester, biotin-N-hydroxysulfosuccinimide ester and biotinoyl-$\epsilon$-aminocaproic acid N-hydroxysuccinimide ester.

A reagent for detecting a ligand in a sample in accordance with the present invention contains a substance which specifically bonds with a ligand labeled by an alkaline phosphatase having the following physical and chemical properties or a ligand labeled by an alkaline phosphatase having the following physical and chemical properties and a reagent for identifying the alkaline phosphatase. Examples of the reagent for detecting the alkaline phosphatase are coloring substrate, fluorescent substrate and luminous substrate.

Examples of the coloring substrate according to the present invention are p-nitrophenyl phosphate, 1-naphtholphthalein monophosphate (Japanese Laid-Open Patent Publication Hei-5-13958), 5-bromo-4-chloro-3-indolyl phosphate and a combination thereof with nitro blue tetrazolium.

Examples of the fluorescent substrate are 4-methylumbelliferone phosphate, phenalenone-6-phosphate and analogous compounds thereof and benzphenalene-6-phosphate and analogous compounds thereof (Japanese Laid-Open Patent Publication Sho-62/190191).

Examples of the luminous substrate are 1,2-dioxetane compounds such as PPD and AMPPD as well as derivatives thereof and mixture thereof with enhancers such as surface-active agents, fluorescent substances and proteins.

Concentration of those substrates of the present invention is 0.01–200 mmoles/l or, preferably, 0.05–50mmoles/l. The enzymatic reaction of the present invention is usually carried out at pH 7–11 but, when an optimum pH is taken into consideration, it is desirable to conduct the enzymatic reaction at pH 8–11. Examples of the buffer applicable are Tris hydrochloride buffer, phosphate buffer, diethanolamine hydrochloride buffer, triethanolamine hydrochloride buffer, bicarbonate buffer, N-methyl-D-glucamine hydrochloride buffer, barbital buffer, glycine sodium hydroxide buffer, 2-amino-2-methylpropanol hydrochloride buffer and amino alcohol type buffer. Concentration of those buffers is 5–200 mmoles/l or, preferably, 20–500 mmoles/l.

Though activity of the enzyme bonded with the reaction product or that bonded with the unreacted substance can be determined by measuring the activity of alkaline phosphatase by a rate method, it can be also determined by the reaction of the above-mentioned substrate with the substance to which the enzyme is bonded followed by detecting said product after stopping the reaction. Examples of the applicable agent for stopping the reaction are alkaline solutions, enzyme inhibitors, chelating agents such as EDTA and inorganic phosphoric acids. When the reaction system is made strongly alkaline after stopping the reaction, sensitivity can be made higher in the case of the substrate such as p-nitrophenyl phosphate and dioxetane compounds (Japanese Laid-Open Patent Publication Hei-2/273199).

It is desirable that metal salts are added to the buffer used for the present invention whereby inactivation of the alkaline phosphatase is prevented. Examples of the metal salts applicable are magnesium salt, cobalt salt, zinc salt, manganese salt and calcium salt and, preferably, magnesium salt and cobalt salt. Preferred concentration of the magnesium salt to be added is 0.05 mmole/l to 10 mmoles/l and examples of the magnesium salt applicable are magnesium acetate, magnesium chloride, magnesium citrate, magnesium sulfate and magnesium complexes such as magnesium ethylenediamine tetraacetate. Preferred concentration of the cobalt salt to be added is 0.02–5 mmoles/l and examples of the applicable cobalt salt are cobalt acetate, cobalt chloride, cobalt citrate, cobalt sulfate and cobalt complexes such as cobalt ethylenediamine tetraacetate. A joint use of magnesium salt and cobalt salt is desirable but it is not essential.

With regard to the surface-active agent which is useful for conducting the present invention, any agent which does not too much inhibit the activity of alkaline phosphatase may be used. Generally, useful surface-active agents are nonionic surface-active agents though amphoteric and ionic ones may be used as well.

An organic solvent which is miscible with water is also possibly used together in the present invention. Examples of the organic solvent are methanol, ethanol, propanol, N,N-dimethylformamide, dimethyl sulfoxide, acetonitrile and hexamethylene phosphamide.

Other compounds may be also added to the reagent of the present invention to conduct the enzymatic reaction smoothly or to keep the activity of the constituting components. Examples of such compounds are stabilizers and excipients. Further, addition of an inactivated type enzyme of alkaline phosphatase is effective for reducing the background and non-specific reactions.

The present invention can be applied not only to the above-mentioned solid phase sandwich immunoassay but also to a measurement of hormone and its receptor utilizing an affinity between hormone and receptor and to a measurement utilizing an affinity between nucleic acid and nucleic acid such as DNA-DNA reaction and DNA-RNA reaction.

A specific example of the present invention for detecting the nucleic acid is that a sample containing nucleic acid (DNA or RNA) is made to act on a material to which the captured oligonucleotide is immobilized, then the detected oligonucleotide which is labeled with an alkaline phosphatase is made to act whereupon a nucleic acid hybridization of the nucleic acid bonding the captured oligonucleotide with the detected labeled oligonucleotide is conducted and, after separating the unreacted detected oligonucleotide, the activity of the alkaline phosphatase of the substance to which a nucleic acid hybridization is carried out is measured whereby the nucleic acid in the sample is detected.

Examples of the nucleic acid in a sample are single- and double-stranded nucleic acid such as DNA and RNA. Examples of the sample are body fluid such as serum, urine and lymph as well as other materials such as various tissues.

In the preparation of the complex of the alkaline phosphatase with DNA or RNA according to the present invention, a method mentioned, for example, in M. Renz and C. Kurz, Nucleic Acids Res., 12(8), 343 (1984) may be applied. For example, alkaline phosphatase is cross-linked with polyethyleneimine and the resulting conjugate is cross-linked with oligonucleotide of DNA or RNA using glutaraldehyde to give a labeled nucleic acid.

Reagents for a direct introduction of amino group or thiol group via a spacer arm to the 5'-terminal or any other chain in the synthesis of oligonucleotides are available in market. It is possible to introduce an alkaline phosphatase into oligonucleotide by bonding such a reagent with the alkaline phosphatase by, for example, means of glutaraldehyde method, maleimide method, carbodiimide method, succinimide ester method and pyridine disulfide method.

An example of the sample is DNA and, when an elongating reaction is carried out using DNA as a template, biotin is incorporated into DNA fragments utilizing a biotinized primer or a biotinized terminator.

After that, the fragments are developed by electrophoresis and then they are made to react with an avidinized alkaline phosphatase or with avidin and then with a biotinized alkaline phosphatase to detect the above-mentioned fragments.

Another specific example of the present invention is a method of analysing the sequence of the nucleic acid in the sample, characterized in that, the alkaline phosphatase having the above-mentioned physical and chemical properties is used as a marker. To determine the sequence of nucleic acids, one can select one of conventional methods which are dideoxytermination, Maxam-Gilbert and so forth. The following procedures are exampled in order to carry out the dideoxytermination method; First, biotin primers are hybridised with the nucleic acids to be determined that are either double-strands or single-strand denatured by alkaline solution, adding a dideoxyribonucleotide (ex. ddATP), four deoxyribonucleotides (dNTPs) and nucleic acid synthesis enzymes (ex. Klenow, T7 DNA polymerase and the like) to proceed the primer-extension reaction and terminate the reaction simultaneously. Then, another three dideoxyribonucleotides (ddCTP, ddGTP and ddTTP) are used in the same reaction as that with the above described ddATP. After subjecting the resulting four reactants to an electrophoresis, alkaline phosphatase with avidin or avidin and then alkaline phosphatase with biotin are reacted with the reactants to detect the extended fragments using chemiluminescence substrates and so forth and determine comparatively the sequence from each lane electrophoresed.

The reagent for analysing the nucleic acid sequence using the above-mentioned nucleic acid which is labeled with alkaline phosphatase includes a reagent for measuring the alkaline phosphatase and DNA or RNA which is bonded with said enzyme.

The present invention is further applicable to an in situ hybridization wherein a nucleic acid hybridization is conducted in cells instead of conducting a nucleic acid hybridization after taking out the nucleic acid from the sample.

According to the present invention, it is possible to afford a novel alkaline phosphatase which exhibits high purity and good stability.

A reagent composition for a binding assay using the alkaline phosphatase of the present invention exhibits a high sensitivity and an excellent storability for long time. In addition, it gives good results with little background in the detection of the aimed substances.

Figure 2:
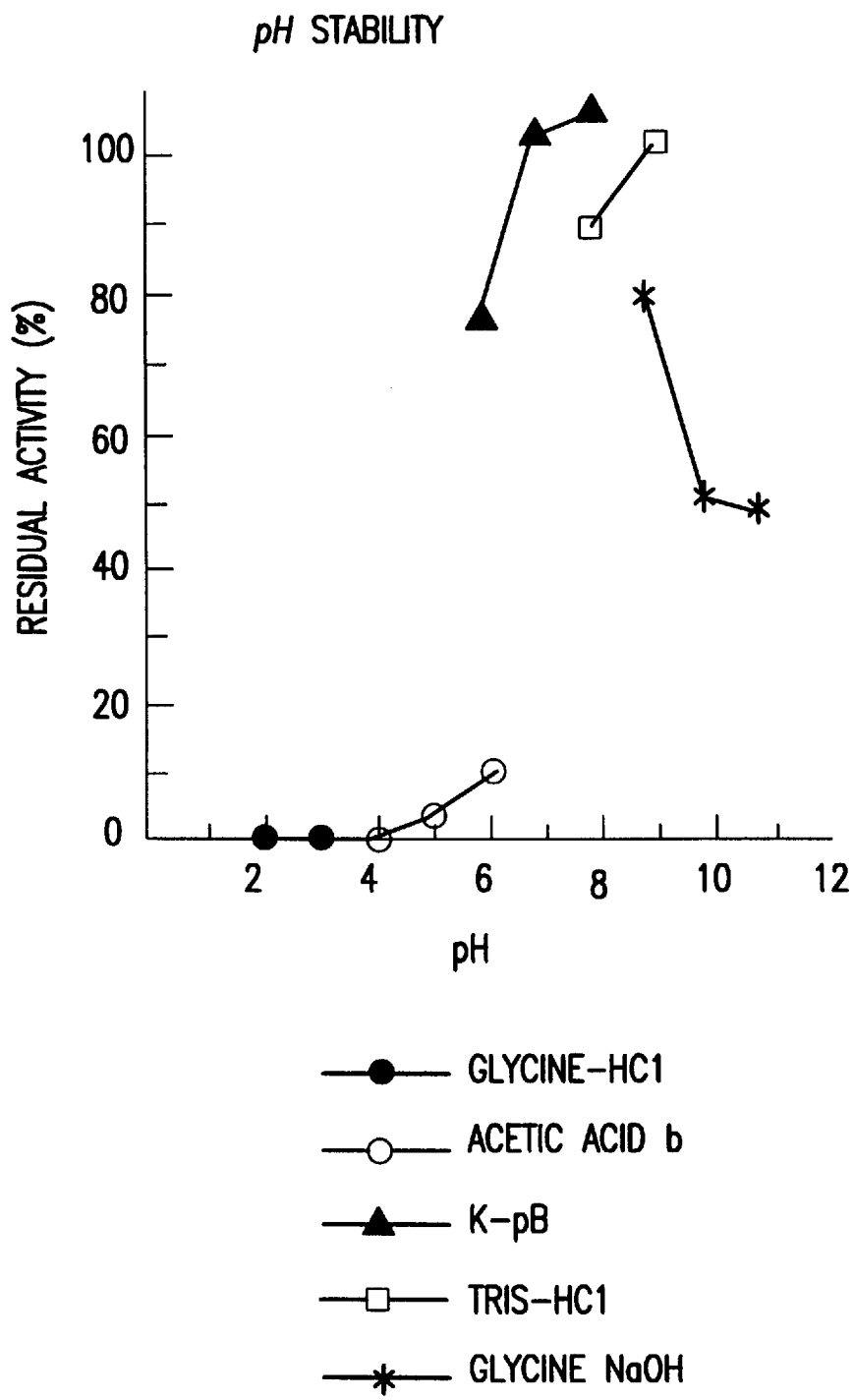
Figure 3:
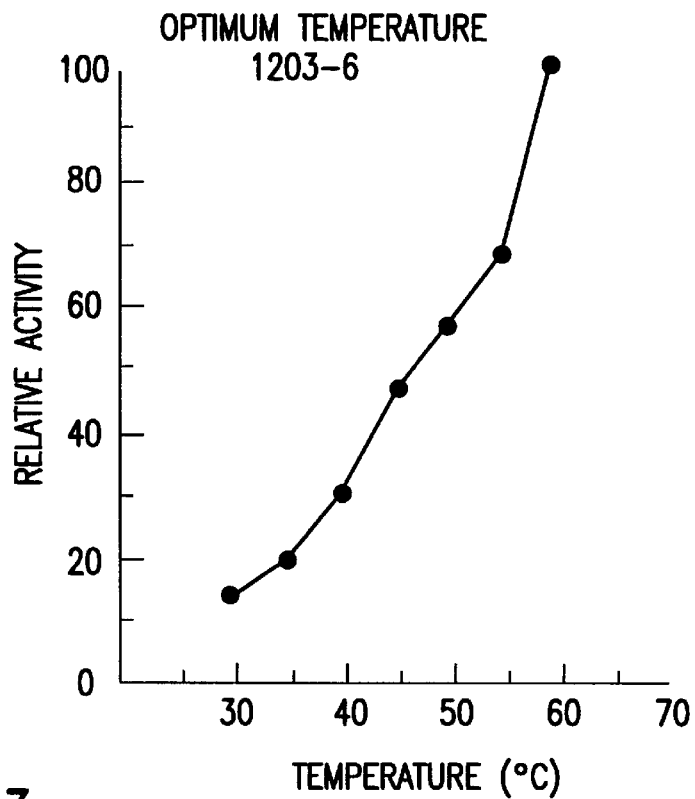
Figure 4:
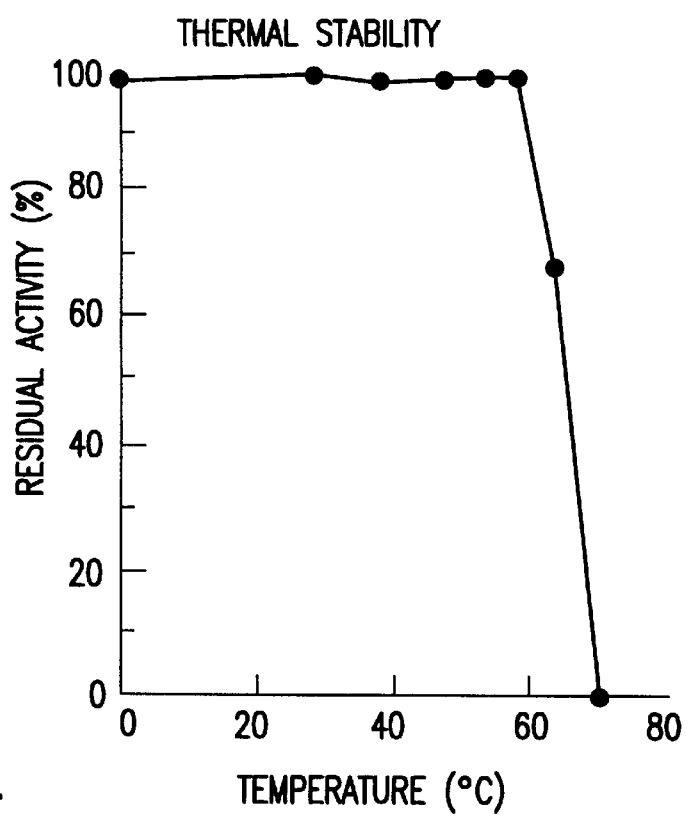
Figure 5:
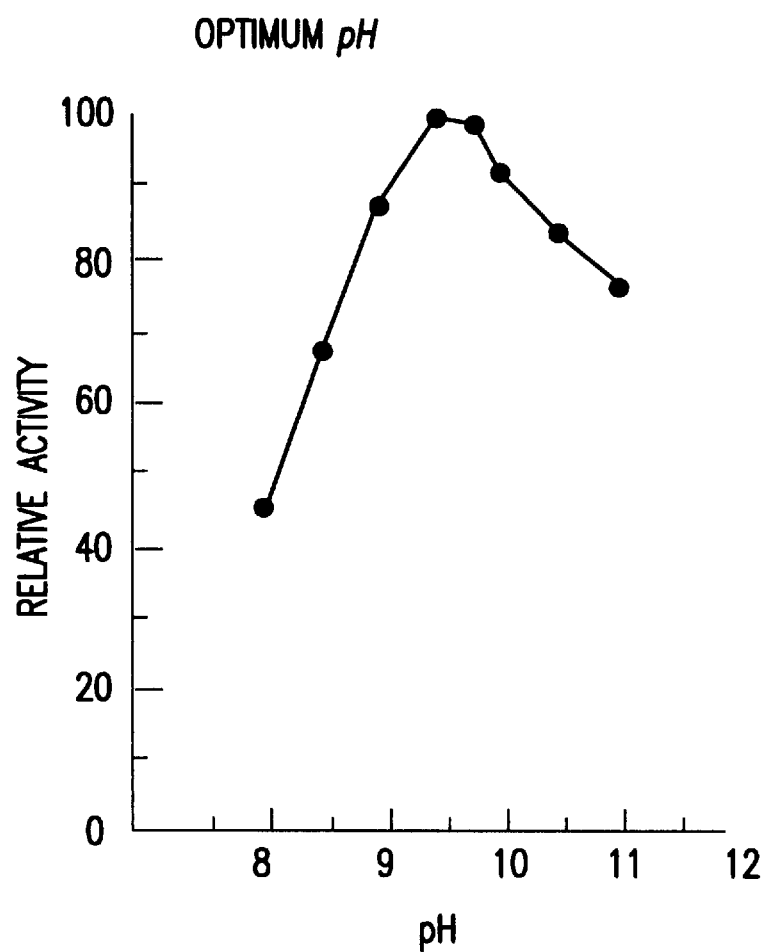
Figure 6:
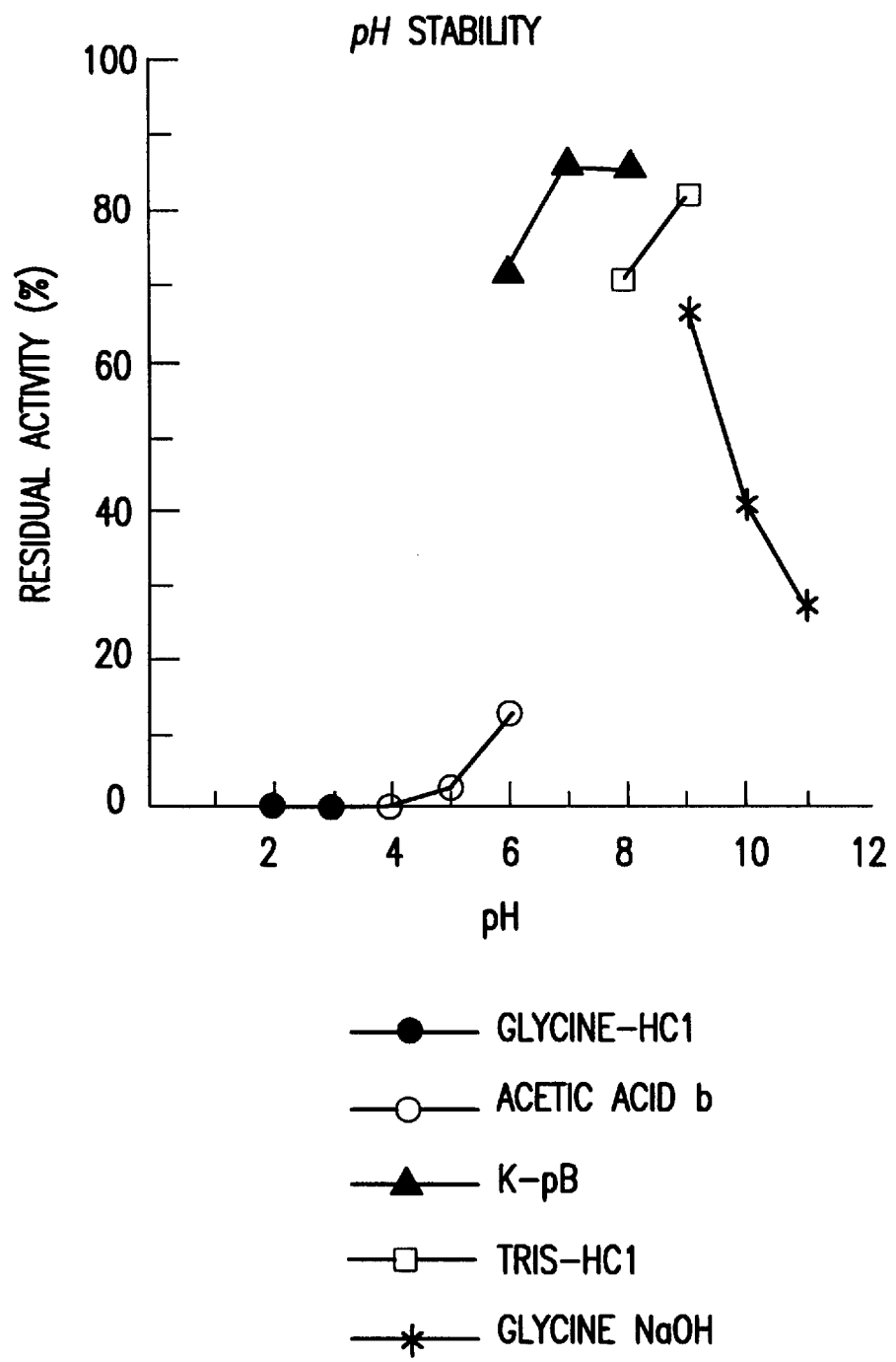
Figure 7:
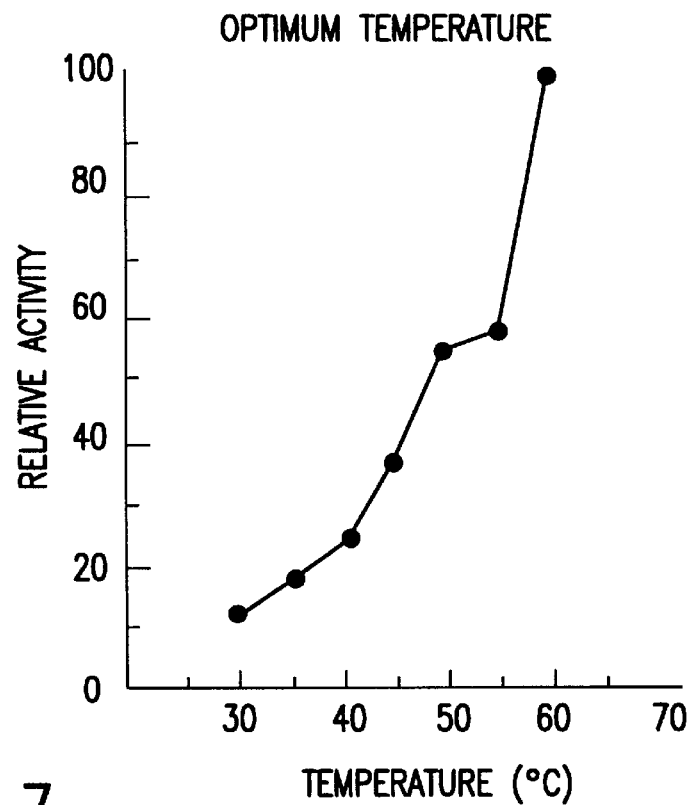
Figure 8:
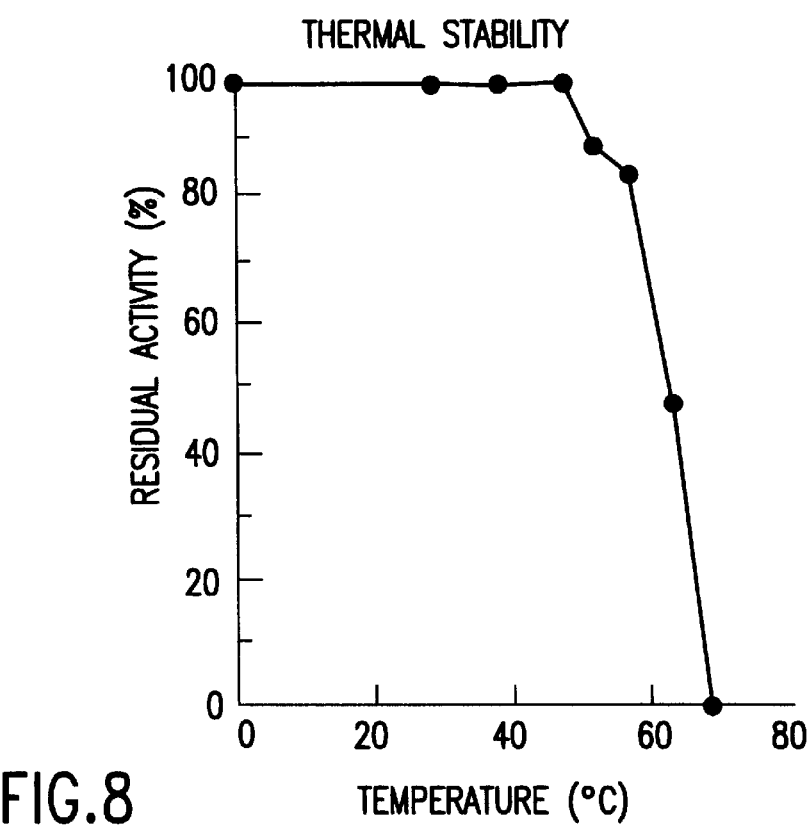
Figure 9:
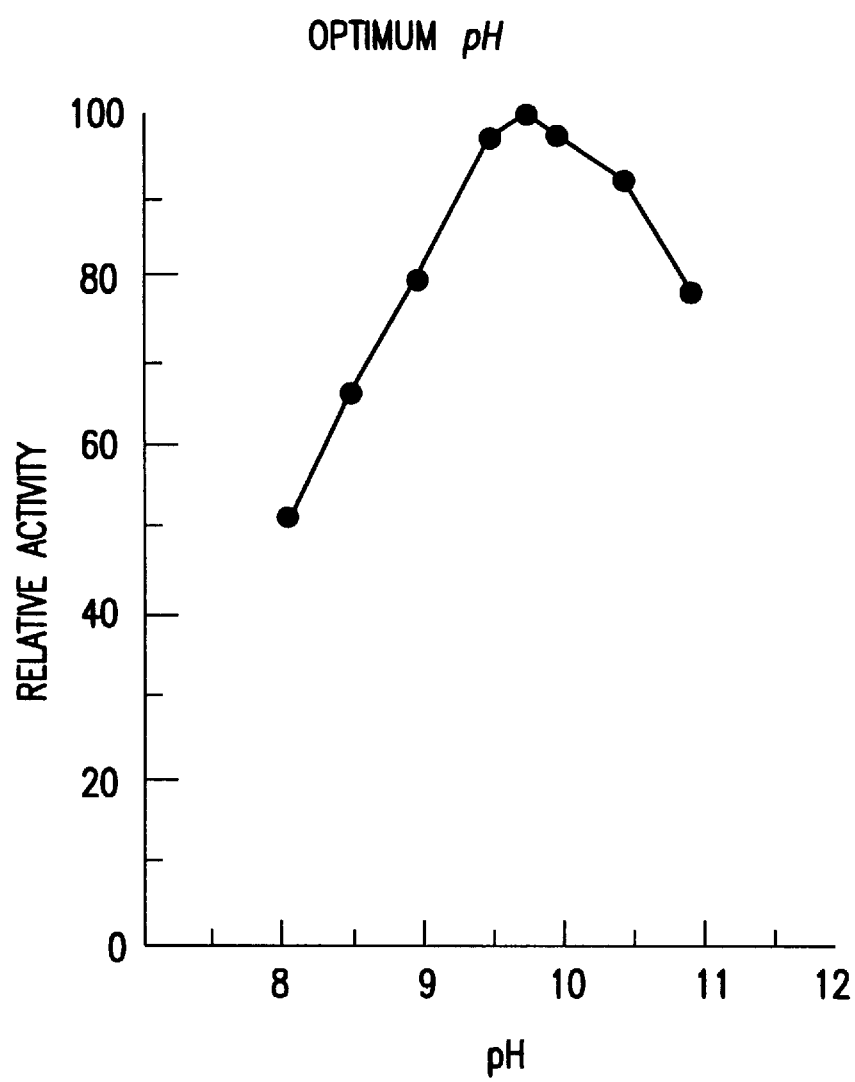
Figure 10:
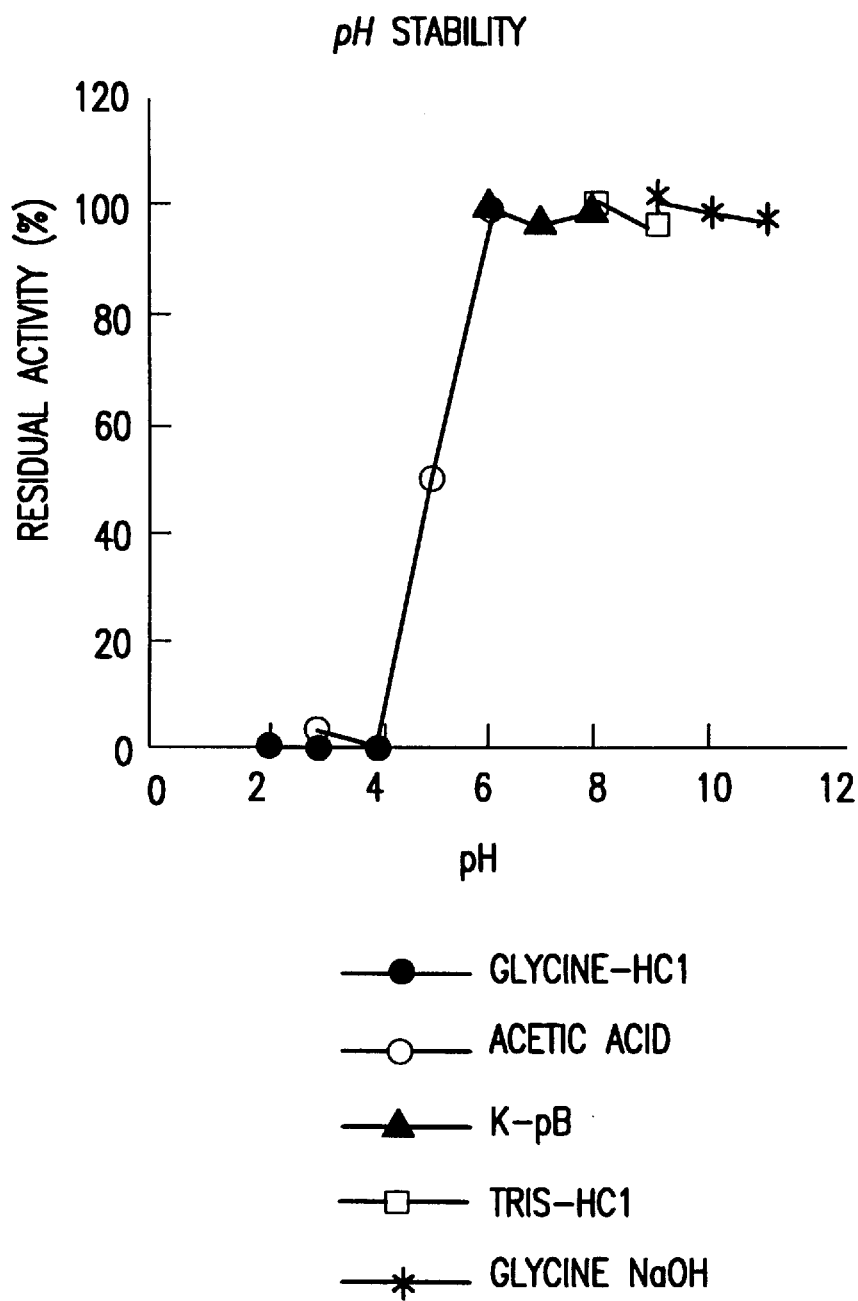
Figure 11:
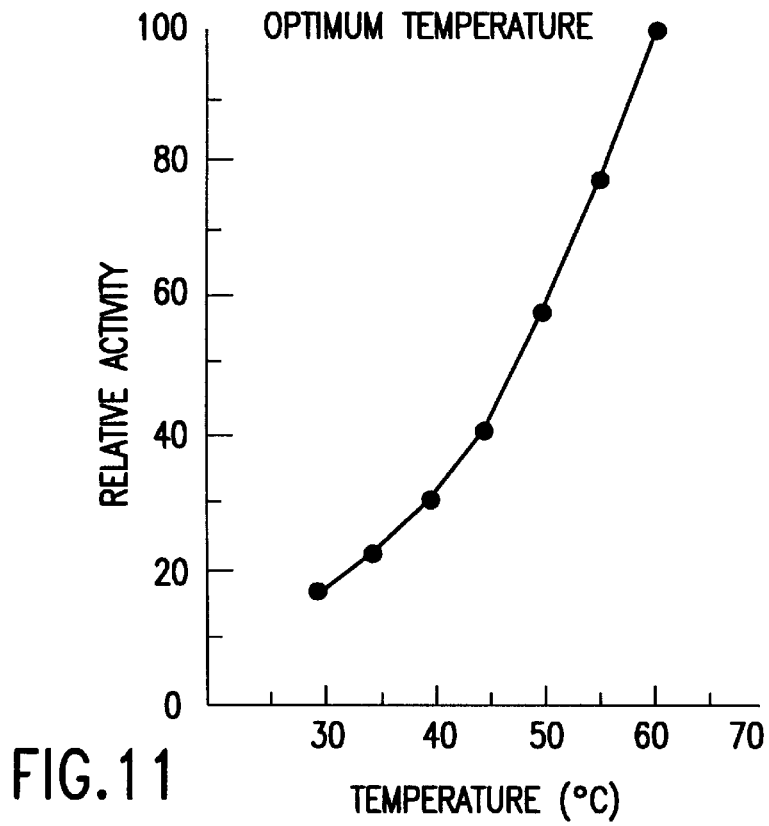
Figure 12:
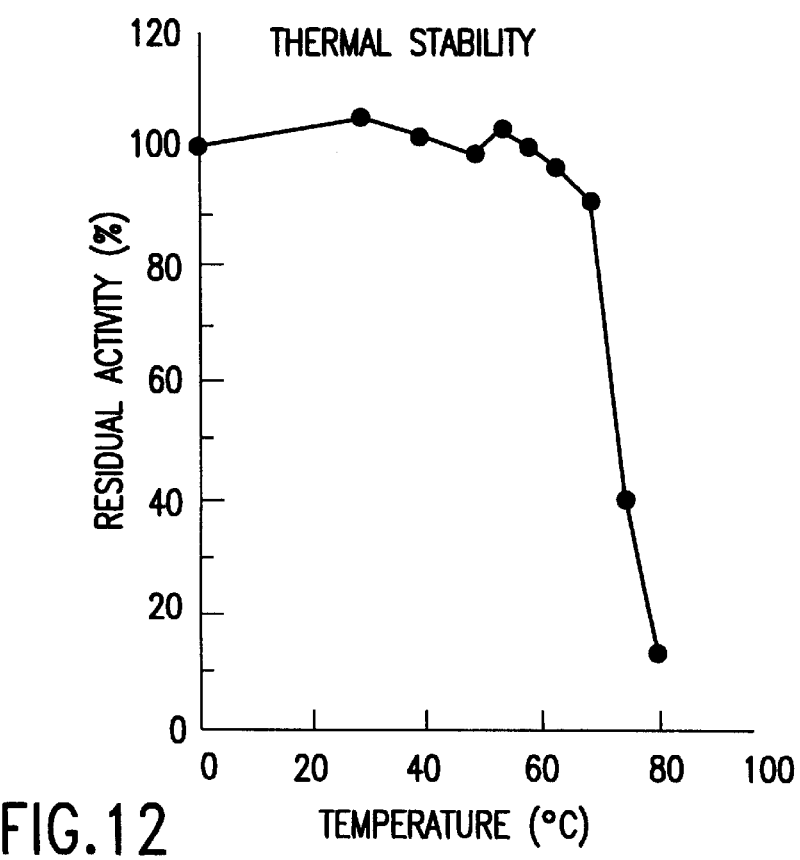
Figure 13:
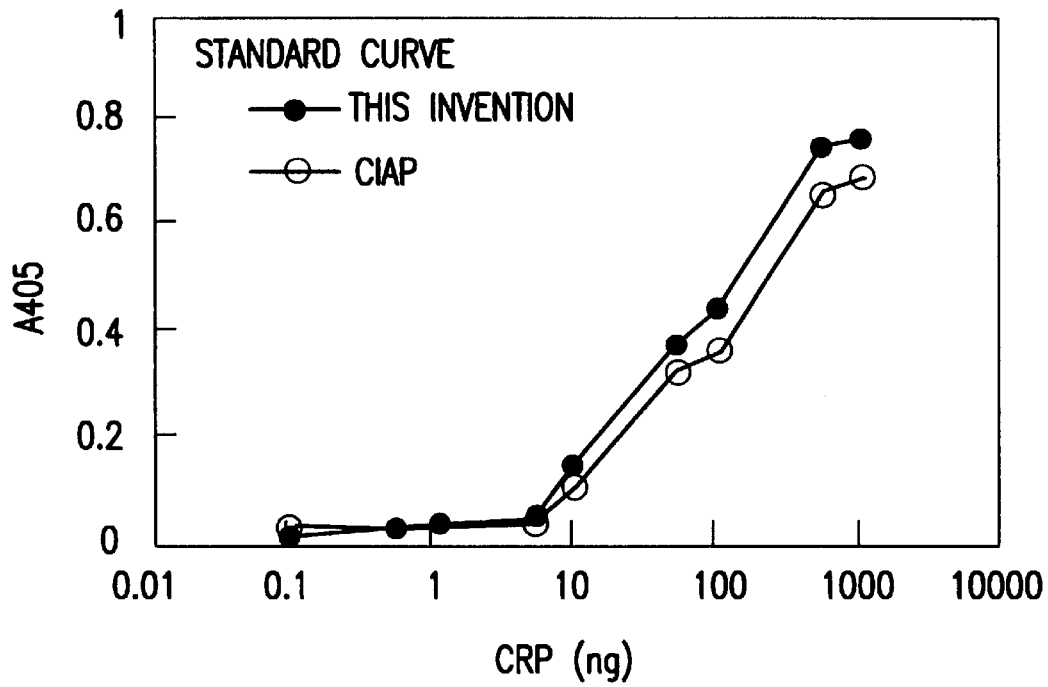
Figure 14:
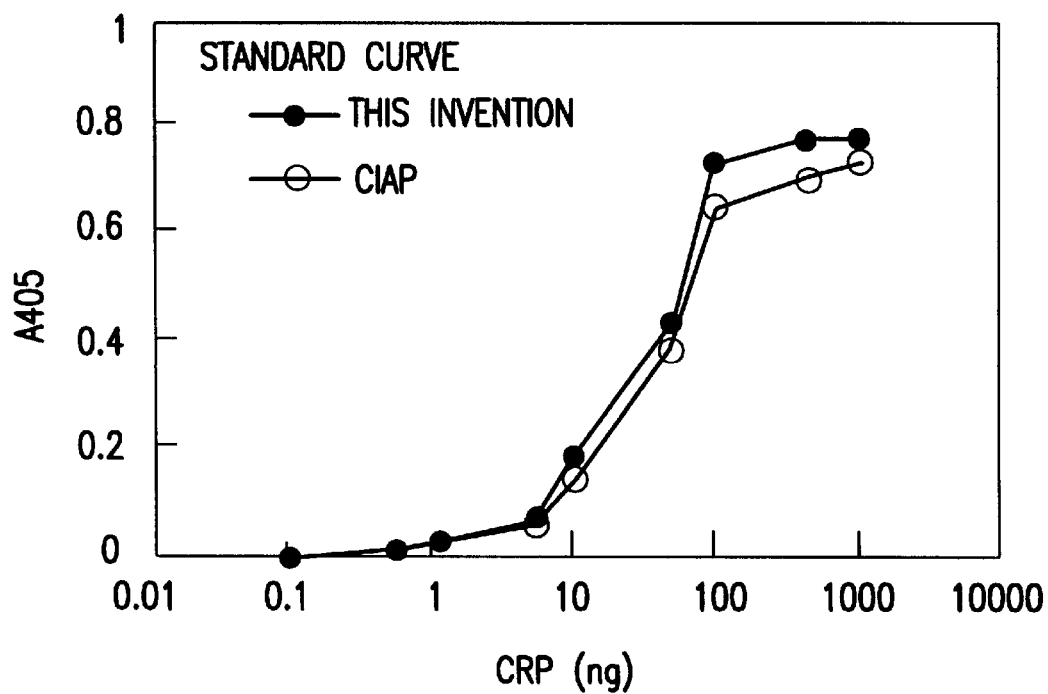
Figure 15:
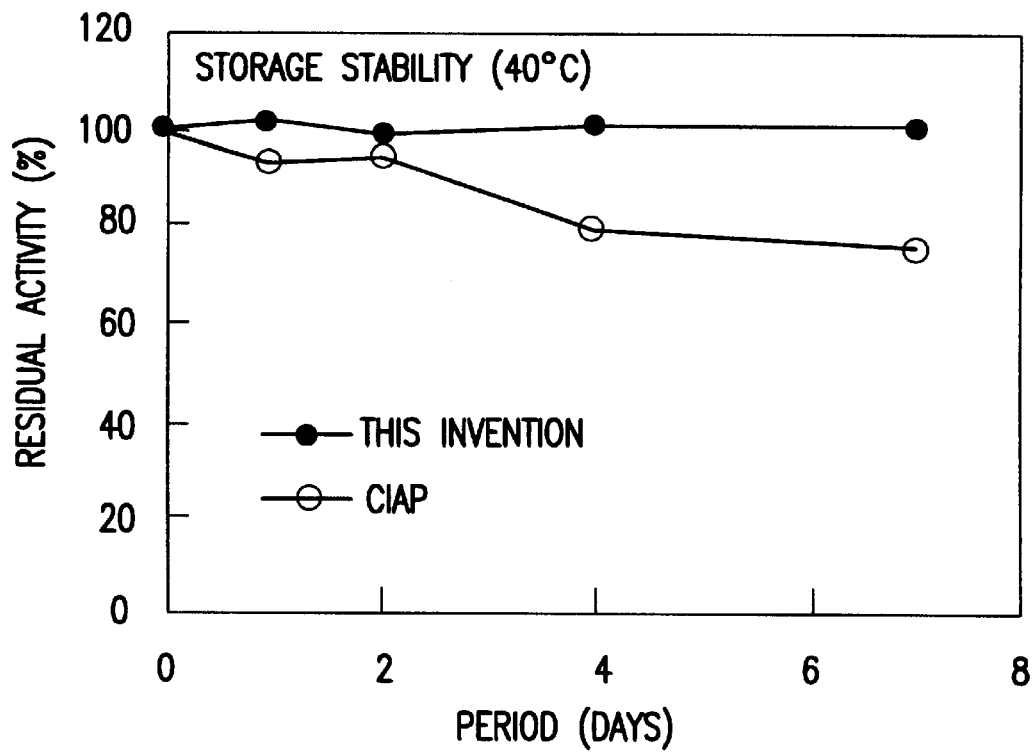
Figure 16:
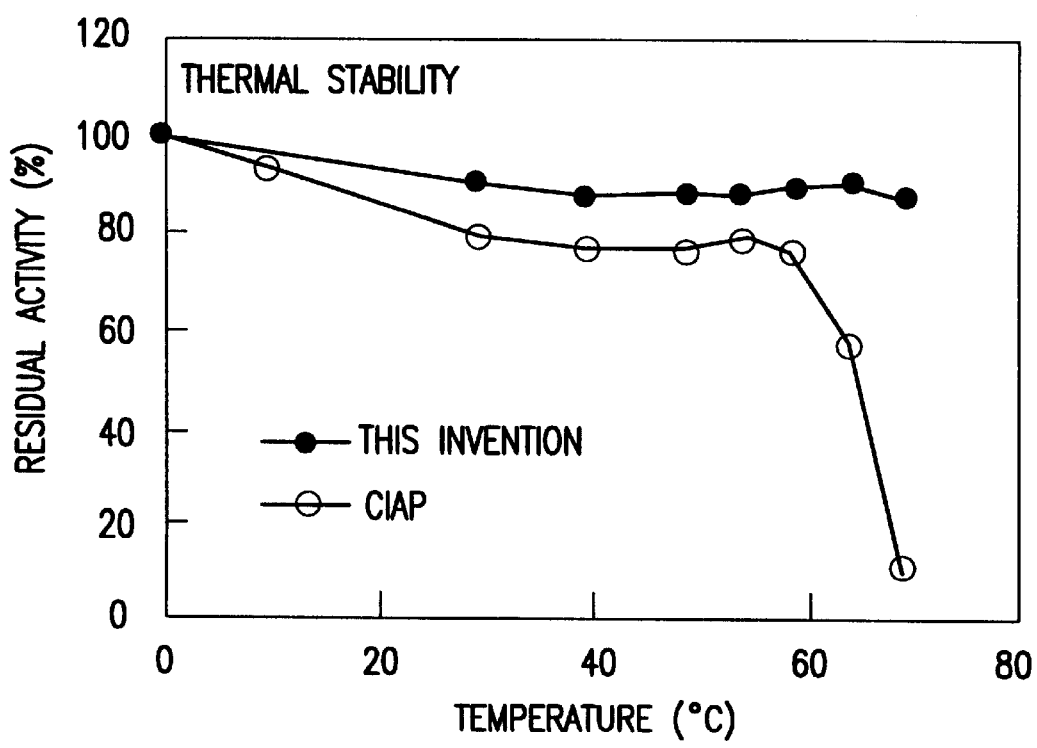
Figure 17:
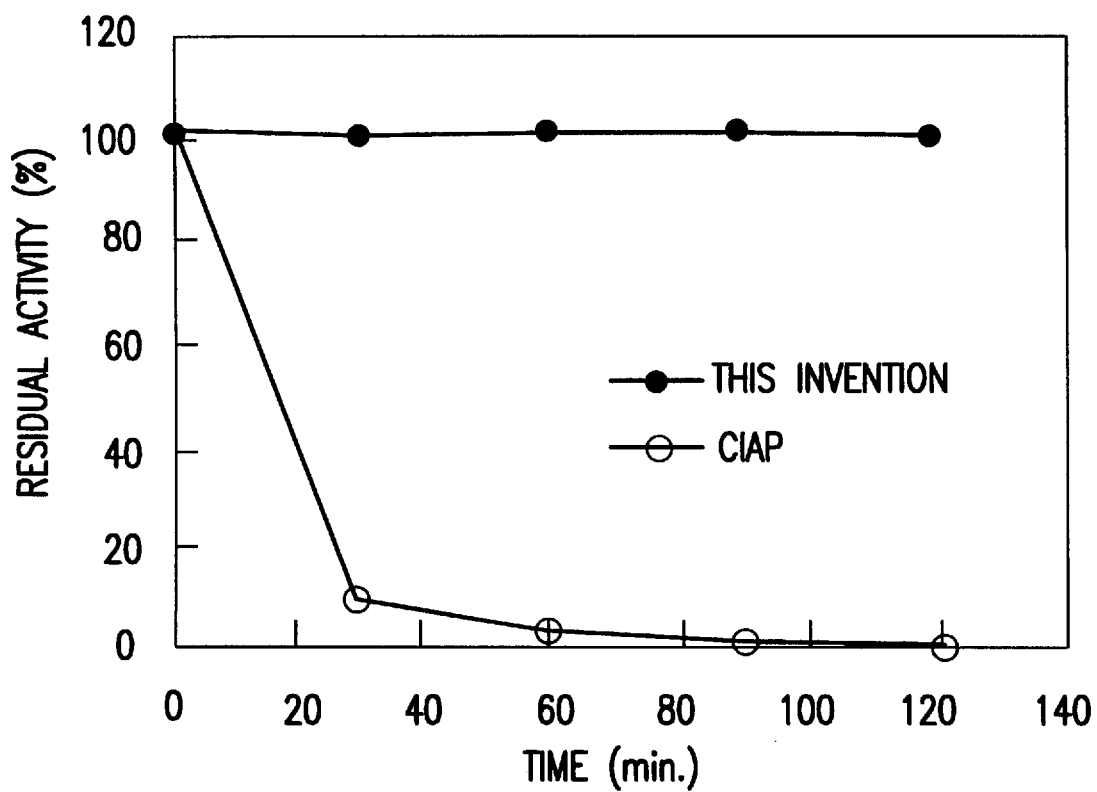

This invention will be further explained by means of the following Examples which refer partly to the accompanying drawings wherein:

FIG. 1 is a graph showing the relation between the reaction pH and relative activity of the enzyme produced by *Bacillus badius* TE3592, FIG. 2 is a graph showing the pH stability of the enzyme produced by Bacillus badius TE3592, FIG. 3 is a graph showing the relation between the reaction temperature and the relative activity of the enzyme produced by *Bacillus badius* TE3592, FIG. 4 is a graph showing the thermal stability of the enzyme produced by *Bacillus badius* TE3592, FIG. 5 is a graph showing the relation between the reaction pH and the relative activity of the enzyme produced by *Bacillus badius* TE3593, FIG. 6 is a graph showing the pH stability of the enzyme produced by *Bacillus badius* TE3593, FIG. 7 is a graph showing the relation between the reaction temperature and the relative activity of the enzyme produced by *Bacillus badius* TE3593, FIG. 8 is a graph showing the thermal stability of the enzyme produced by *Bacillus badius* TE3593, FIG. 9 is a graph showing the relation between the reaction pH and the relative activity of the enzyme produced by *Bacillus badius* TE3597, FIG. 10 is a graph showing the pH stability of the enzyme produced by *Bacillus badius* TE3597, FIG. 11 is a graph showing the relation between the reaction temperature and the relative activity of the enzyme produced by *Bacillus badius* TE3597, FIG. 12 is a graph showing the thermal stability of the enzyme produced by *Bacillus badius* TE3597, FIG. 13 shows a comparison of calibration curves of human CRP using goat anti-human CRPIgG labeled with the enzyme of the present invention and that labeled with CIAP, FIG. 14 shows a comparison of calibration curves of human CRP using goat anti-human CRP Fab' labeled with the enzyme of the present invention and that labeled with CIAP, FIG. 15 shows a comparison of the stabilities upon storage of streptoavidin labeled with the enzyme of the present invention and that labeled with CIAP, FIG. 16 shows a comparison of thermal stabilities of biotin labeled with the enzyme of the present invention and that labeled with CIAP, and FIG. 17 shows thermal stability of the probe labeled with the enzyme of the present invention and that labeled with CIAP.

EXAMPLE 1

A medium (100 ml) containing 3.0% of glycerol, 1.0% of polypeptone, 0.1% of yeast extract, 0.02% of magnesium sulfate, 0.002% of monopotassium phosphate and 0.3% of sodium chloride was transferred to a 500 ml Sakaguchi's flask and autoclaved at 121° C. for 15 minutes. One platinum loop of Bacillus badius TE3592 (FERM BP-5329) was inoculated as a seed and cultured at 30° C. for 20 hours to prepare a seed culture liquid. Then six liters of the same medium was transferred to a 10 liter jar fermentor, autoclaved at 121° C. for 15 minutes, allowed to cool and 100 ml of the seed culture liquid was added thereto followed by culturing at 300 rpm and 30° C. with 2 liters/minute of aeration for 20 hours. The resulting culture liquid was centrifuged to give a supernatant liquid. This liquid was purified to an extent of 2,300 U/mg of specific activity by means of fractionation with sodium sulfate, DEAE-Sepharose chromatography, phenyl Sepharose chromatography and gel filtration with Sephadex G-200.

The resulting alkaline phosphatase had the following characteristics.

1. It catalyzed the following reaction.

Orthophosphoric acid monoester+$H_2O$→Alcohol+Orthophosphoric acid

2. Substrate specificity.
   (shown in Table 1)

TABLE 1

| Compounds | Relative Activity |
|---|---|
| p-Nitrophenyl phosphate | 100 |
| 4-Methylumbelliferyl phosphate | 87.6 |
| NADP | 15.4 |
| DL-α-Glycerophosphate | 37.9 |
| β-Glycerophosphate | 49.7 |
| Phenyl phosphate | 140 |
| Phosphoryl choline | 2.96 |
| Phosphoethanolamine | 44.4 |
| Glucose-1-phosphate | 0 |
| Glucose-6-phosphate | 14.8 |

3. Km value.
   The Km value to p-nitrophenol was 0.34 mM.
4. Optimum pH.
   Its enzymatic activity in 0.97M diethanolamine buffer (pH: 8.0–11.0) was measured. The result was as shown in FIG. 1 and the optimum pH was 9–10.
5. Stable pH.
   It was stored in glycine hydrochloride buffer (pH: 2–3), acetate buffer (pH: 3–6), potassium phosphate buffer (pH: 6–8), Tris hydrochloride buffer (pH: 8–9) and glycine-NaOH buffer (pH: 9–10) at 25° C. for 16 hours and the residual activities were measured. The result was as shown in FIG. 2 and the stable pH was 6–9.
6. Optimum temperature.
   Its enzymatic activities at various temperature were measured. The result was as shown in FIG. 3 and the optimum temperature was not lower than 60° C.
7. Thermal stability.
   The enzyme of the present invention was warmed for 30 minutes in a 50 mM Tris hydrochloride buffer (pH: 7.5) containing 1.0 mM of $MgCl_2$ and 0.1 mM of $CoCl_2$ and the residual enzymatic activity was measured. The result was as given in FIG. 4 and the enzyme was found to be stable until 60° C.
8. Activators and stabilizers.
   $Mg^{++}$ and $Co^{++}$ were found to be essential.
9. Molecular weight.
   140,000–150,000 (gel filtration)

65,000–67,000 (SDS-PAGE)
10. Sugar content.
    No sugar was detected.

EXAMPLE 2

A medium (100 ml) containing 3.0% of glycerol, 1.0% of polypeptone, 0.1% of yeast extract, 0.02% of magnesium sulfate, 0.002% of monopotassium phosphate and 0.3% of sodium chloride was transferred to a 500 ml Sakaguchi's flask and autoclaved at 121° C. for 15 minutes. One platinum loop of Bacillus badius TE3593 (FERM BP-5330) was inoculated as a seed and cultured at 30° C. for 20 hours to prepare a seed culture liquid. Then six liters of the same medium was transferred to a 10 liter jar fermentor, autoclaved at 121° C. for 15 minutes, allowed to cool and 100 ml of the seed culture liquid was added thereto followed by culturing at 300 rpm and 30° C. with 2 liters/minute of aeration for 20 hours. The resulting culture liquid was centrifuged to give a supernatant liquid. This liquid was purified to an extent of 2,790 U/mg of specific activity by means of fractionation with sodium sulfate, DEAE-Sepharose chromatography, phenyl Sepharose chromatography and gel filtration with Sephadex G-200.

The resulting alkaline phosphatase had the following characteristics.

1. It catalyzed the following reaction.

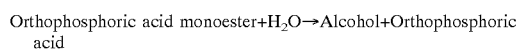

Orthophosphoric acid monoester+$H_2O$→Alcohol+Orthophosphoric acid

2. Substrate specificity.
   (shown in Table 2)

TABLE 2

| Compounds | Relative Activity |
|---|---|
| p-Nitrophenyl phosphate | 100 |
| 4-Methylumbelliferyl phosphate | 108 |
| NADP | 90.5 |
| DL-α-Glycerophosphate | 71.4 |
| β-Glycerophosphate | 78.1 |
| Phenyl phosphate | 180 |
| Phosphoryl choline | 3.81 |
| Phosphoethanolamine | 73.8 |
| Glucose-1-phosphate | 1.44 |
| Glucose-6-phosphate | 44.3 |

3. Km value.
   The Km value to p-nitrophenol was 0.26 mM.
4. Optimum pH.
   Its enzymatic activity in 0.97M diethanolamine buffer (pH: 8.0–11.0) was measured. The result was as shown in FIG. 5 and the optimum pH was 9–10.
5. Stable pH.
   It was stored in glycine hydrochloride buffer (pH: 2–3), acetate buffer (pH: 3–6), potassium phosphate buffer (pH: 6–8), Tris hydrochloride buffer (pH: 8–9) and glycine-NaOH buffer (pH: 9–10) at 25° C. for 16 hours and the remaining activities were measured. The result was as shown in FIG. 6 and the stable pH was 6–9.
6. Optimum temperature.
   Its enzymatic activities at various temperature were measured. The result was as shown in FIG. 7 and the optimum temperature was not lower than 60° C.
7. Thermal stability.
   The enzyme of the present invention was warmed for 30 minutes in a 50 mM Tris hydrochloride buffer (pH: 7.5) containing 1.0 mM of MgCl$_2$ and 0.1 mM of CoCl$_2$ and the remained enzymatic activity was measured. The result was as given in FIG. 8 and the enzyme was found to be stable until 60° C.

8. Activators and stabilizers.
   Mg$^{++}$ and Co$^{++}$ were found to be essential.
9. Molecular weight.
   140,000–150,000 (gel filtration)
   65,000–67,000 (SDS-PAGE)
10. Sugar content.
    No sugar was detected.

EXAMPLE 3

A medium (100 ml) containing 3.0% of glycerol, 1.0% of polypeptone, 0.1% of yeast extract, 0.02% of magnesium sulfate, 0.002% of monopotassium phosphate and 0.3% of sodium chloride was transferred to a 500 ml Sakaguchi's flask and autoclaved at 121° C. for 15 minutes. One platinum loop of *Bacillus badius* TE3597 (FERM BP-5120) was inoculated as a seed and cultured at 30° C. for 20 hours to prepare a seed culture liquid. Then six liters of the same medium was transferred to a 10 liter jar fermentor, autoclaved at 121° C. for 15 minutes, allowed to cool and 100 ml of the seed culture liquid was added thereto followed by culturing at 300 rpm and 30° C. with 2 liters/minute of aeration for 20 hours. The resulting culture liquid was centrifuged to give a supernatant liquid. This liquid was purified to an extent of 2,300 U/mg of specific activity by means of fractionation with sodium sulfate, DEAE-Sepharose chromatography, phenyl Sepharose chromatography and gel filtration with Sephadex G-200.

The resulting alkaline phosphatase had the following characteristics.

1. It catalyzed the following reaction.

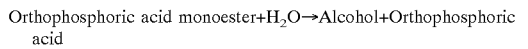

Orthophosphoric acid monoester+H$_2$O→Alcohol+Orthophosphoric acid

2. Substrate specificity.
   (shown in Table 3)

TABLE 3

| Compounds | Relative Activity |
| --- | --- |
| p-Nitrophenyl phosphate | 100 |
| 4-Methylumbelliferyl phosphate | 98.0 |
| NADP | 15.4 |
| DL-α-Glycerophosphate | 67.0 |
| β-Glycerophosphate | 67.5 |
| Phenyl phosphate | 167 |
| Phosphoryl choline | 6.50 |
| Phosphoethanolamine | 67.0 |
| Glucose-1-phosphate | 25.0 |
| Glucose-6-phosphate | 34.5 |

3. Km value.
   The Km value to p-nitrophenol was 0.28 mM.
4. Optimum pH.
   Its enzymatic activity in 0.97M diethanolamine buffer (pH: 8.0–11.0) was measured. The result was as shown in FIG. 9 and the optimum pH was 9.5–10.
5. Stable pH.
   It was stored in glycine hydrochloride buffer (pH: 2–3), acetate buffer (pH: 3–6), potassium phosphate buffer (pH: 6–8), Tris hydrochloride buffer (pH: 8–9) and glycine-NaOH buffer (pH: 9–10) at 25° C. for 16 hours and the residual activities were measured. The result was as shown in FIG. 10 and the stable pH was 6–11.
6. Optimum temperature.
   Its enzymatic activities at various temperature were measured. The result was as shown in FIG. 11 and the optimum temperature was not lower than 60° C.
7. Thermal stability.
   The enzyme of the present invention was warmed for 30 minutes in a 50 mM Tris hydrochloride buffer (pH: 7.5) containing 1.0 mM of MgCl$_2$ and 0.1 mM of CoCl$_2$ and the remained enzymatic activity was measured. The result was as given in FIG. 12 and the enzyme was found to be stable until 70° C.
8. Activators and stabilizers.
   Mg$^{++}$ and Co$^{++}$ were found to be essential.
9. Molecular weight.
   140,000–150,000 (gel filtration)
   65,000–67,000 (SDS-PAGE)
10. Sugar content.
    No sugar was detected.

Comparative Example 1

Properties of the enzymes of the present invention were compared with those of known enzymes in the following table.

TABLE 4

| | Calf Intestine | Bacillus sp. OK-1 | Bacillus liqueniformis MC14 | Bacillus Badius TE3592 |
| --- | --- | --- | --- | --- |
| Activators | Mg$^{++}$ | Co$^{++}$ | Co$^{++}$ | Mg$^{++}$, Co$^{++}$ |
| Thermal stability | ≦45° C. | ≦60° C. | ≦60° C. | ≦60° C. |
| Optimum temperature | 35–45° C. | 50° C. | | ≧60° C. |
| Stable pH | 6–11 | 5–12 | | 6–9 |
| Optimum pH | 10 | 11 | | 9–10 |
| Specific activity (temp) | 3000–5000 U/mg | 1650 U/mg (37° C.) | 2115.9 U/mg (55° C.) | 2300 U/mg (37° C.) |
| Sugar chain | present | none | none | none |
| Km value (p-nitrophenyl phosphate) | | 0.037 mM | | 0.34 mM |
| Molecular weight (gel filtration) | 80,000 | 110,000 | 110,000 | 140,000–150,000 |
| References | JP Laid Open Pat Pub Sho-60/180584 | Agr. Biol. Chem. 52 (7) 1643 (1988) | J. Gen. Microbiol. 132, 2387 (1986) | (this invention) |

| | Bacillus Badius TE3593 | Bacillus Badius TE3597 |
| --- | --- | --- |
| Activators | Mg$^{++}$, Co$^{++}$ | Mg$^{++}$, Co$^{++}$ |
| Thermal stability | ≦60° C. | ≦70° C. |
| Optimum temperature | ≧60° C. | ≧60° C. |
| Stable pH | 6–9 | 6–11 |
| Optimum pH | 9–10 | 9.5–10 |
| Specific activity (temp) | 2790 U/mg (37° C.) | 2300 U/mg (37° C.) |
| Sugar chain | none | none |
| Km value (p-nitrophenyl phosphate) | 0.26 mM | 0.284 mM |
| Molecular weight (gel filtration) | 140,000–150,000 | 140,000–150,000 |
| References | (this invention) | (this invention) |

EXAMPLE 4

(1) Preparation of goad anti-human CRPIgG labeled with an alkaline phosphatase.

A 25% glutaraldehyde solution (35 μl) was added to 2.5 ml of 50 mM phosphate buffer (pH: 7.2; containing 1 mM MgCl$_2$ and 0.1 mM CoCl$_2$) containing 5 mg of the alkaline phosphatase of Referential Example 1 and an incubation was conducted at 25° C. for 50 minutes. Then 0.5 ml of 50 mM phosphate buffer (pH: 7.2) containing 2.5 mg of goat anti-human CRPIgG fraction (manufactured by Nippon Biotest Laboratory) was added thereto and an incubation was conducted at 25° C. for 75 minutes more. After that, 150 µl of 2M Tris/HCl (pH: 8.7) was added, the mixture was stirred at 4° C. for 30 minutes, 150 µl of aqueous solution containing 150 mg of NaBH$_4$ was added and an incubation was conducted at 4° C. for 15 hours. The resulting mixture was purified by means of a high performance liquid chromatography using Superdex™ 200 (manufactured by Farmacia) (using 50 mM Tris/HCl [pH: 8.0] as an eluting liquid containing 0.1M NaCl, 1 mM MgCl$_2$, 0.1 mM CoCl$_2$ and 0.1% of NaN$_3$) and the first peak was obtained as an enzyme-labeled antibody.

(2) Calibration curve of human CRP.

Human CRP (0–1000 ng/ml) (1 ml) was added to one polystyrene bead coated with goat anti-human CRPIgG fractions (manufactured by Nippon Biotest Laboratory) and an incubation was conducted at 30° C. for one hour. Then the solid phase was washed with PBS thrice, 1 ml of an enzyme-labeled antibody diluted to an extent of 1 U/ml in terms of an alkaline phosphatase activity was added and an incubation was conducted at 30° C. for one hours. This was further washed with PBS thrice, a 1M diethanolamine buffer (pH: 9.8) containing 11 mM p-nitrophenyl phosphate and 5 mM MgCl$_2$ was added, a reaction was conducted at 37° C. for 30 minutes, 2 ml of 0.5N NaOH was added to stop the reaction and the absorption at 405 nm was measured to prepare a calibration curve (FIG. 13).

Comparative Example 2

A 25% glutaraldehyde solution (150 µl) was added to 2.5 ml of a 50 mM phosphate buffer (pH: 7.2) containing 5 mg of an alkaline phosphatase derived from calf intestine and the same operations as in Example 1 were conducted to prepare an enzyme-labeled antibody.

The above-prepared enzyme-labeled antibody was used for preparing a calibration curve for human CRP by the same manner as in Example 1 (FIG. 13). Ratio (S/N ratio) of the absorption of the specific coloration (10 ng/ml of human CRP) to that of the blank (0 ng/ml of human CRP) was 1.25 for the alkaline phosphatase of the present invention while that for CIAP was 5.13. Thus, the alkaline phosphatase of the present invention had less non-specific adsorption.

EXAMPLE 5

(1) Preparation of sheep anti-human CRP Fab' labeled with alkaline phosphatase.

A 0.1M phosphate buffer (pH: 6.0) (100 ml) containing 0.1M 2-mercaptoethylamine and 10 mM EDTA was added to 1 ml of 0.1M phosphate buffer (pH: 6.0) containing 5 mg of sheep anti-human CRP F(ab')$_2$ (manufactured by Binding Site) and an incubation was conducted at 37° C. for 90 minutes. Said mixture was desalted with a 0.1M phosphate buffer (pH: 6.0) containing 5 mM EDTA and concentrated to 0.5 ml. On the other hand, 10 µl of dimethylformamide containing 0.1 mg of N-succinimidyl-4-(N-maleimidomethyl)-cyclohexane-1-carboxylate was added to 500 µl of a 30 mM triethanolamine buffer (pH: 7.6; containing 1 mM MgCl$_2$ and 0.1 mM CoCl$_2$) containing 2.5 mg of the alkaline phosphatase of the present invention and an incubation was conducted at 30° C. for 30 minutes. The resulting solution was desalted with a 0.1M Tris hydrochloride buffer (pH: 7.0) containing 1 mM MgCl$_2$ and 0.1 mM CoCl$_2$ and concentrated to 0.5 ml.

Maleimidated alkaline phosphatase was added to the sheep anti-human CRP Fab' prepared as such and an incubation was conducted at 4° C. for 20 hours. Then 50 µl of 10 mM 2-mercaptoethylamine was added thereto and an incubation was conducted at 25° C. for 20 minutes. The resulting mixture was purified by Superdex™ 200 and the first peak was collected as an enzyme-labeled antibody.

(2) Calibration curve of human CRP.

Human CRP (0–1,000 ng/ml) (1 ml) was added to one polystyrene bead coated with goat anti-human CRPIgG fractions (manufactured by Nippon Biotest Laboratory) and an incubation was conducted at 30° C. for one hour. Then the solid phase was washed with PBS thrice, 1 ml of an enzyme-labeled antibody diluted to an extent of 1 U/ml in terms of the alkaline phosphatase activity and an incubation was conducted at 30° C. for one hour. This was further washed with PBS thrice, a 1M diethanolamine buffer (pH: 9.8) containing 11 mM p-nitrophenyl phosphate and 5 mM MgCl$_2$ was added, a reaction was conducted at 37° C. for 30 minutes, then the reaction was stopped by adding 2 ml of 0.5N NaOH thereto and the absorbance at 405 nm was measured whereby a calibration curve was prepared (FIG. 14).

Comparative Example 3

The same operations as in Example 2 were conducted for 500 µl of a 30 mM triethanolamine buffer (pH: 7.6) (containing 1 mM MgCl$_2$, 0.1 mM ZnCl$_2$ and 3M NaCl) containing 2.5 mg of CIAP to give an enzyme-labeled antibody.

The above-prepared enzyme-labeled antibody was used and a calibration curve for human CRP was prepared by the same manner as in Example 1 (FIG. 14). Ratio (S/N ratio) of the absorbance of a specific coloration (10 ng/ml human CRP) to that of a blank (0 ng/ml human RRP) was 55.2 for the alkaline phosphatase of the present invention while said ratio was 34.8 for CIAP. Thus, the alkaline phosphatase of the present invention showed less non-specific adsorption.

EXAMPLE 6

(1) Preparation of an alkaline phosphatase labeled with streptoavidin.

Dimethylformamide (10 µl) containing 0.1 mg of S-acetylmercaptosuccinic anhydride was added to 600 µl of 0.1M phosphate buffer (pH: 7.5) containing 4 mg of streptoavidin and an incubation was conducted at 30° C. for 30 minutes. Then 20 µl of 1M EDTA (pH: 7.0), 120 µl of 0.1M Tris/HCl (pH: 7.0) and 120 µl of 1M hydroxylamine hydrochloride were added thereto, an incubation was conducted at 30° C. for five minutes, the mixture was desalted with a 0.1M phosphate buffer (pH: 6.0) and concentrated to 600 µl. The mercaptosuccinylated streptoavidin (100 µl) prepared as such was added to a solution of a maleimidated alkaline phosphatase prepared in Example 2, the mixture was incubated at 4° C. for 20 hours, the resulting mixture was purified by Superdex™ 200 and the first peak was taken as an enzyme-labeled streptoavidin.

Comparative Example 4

Enzyme-labeled streptoavidin was prepared from CIAP by the same method as in Example 6.

Biotinyl BSA (0–5 ng) was applied to immobilon (Millipore), blocked with PBS containing 1% of casein and incubated with 0.3 U/ml of the enzyme-labeled streptoavidin of the present invention and CIAP-labeled streptoavidin at 30° C. for one hour. Then this was made to react with a 1M diethanolamine buffer (pH: 9.8; containing 5 mM $MgCl_2$) containing PPD (a luminous substrate) and a detection was conducted by sensitizing on an X-ray film. Both enzyme-labeled one of the present invention and CIAP-labeled one were able to detect 0.5 ng of biotinylated streptoavidin.

Then the enzyme-labeled streptoavidin of the present invention and the CIAP-labeled streptoavidin were stored at 40° C. for seven days in 50 mM Tris/HCl (pH: 7.5) containing 1 mM $MgCl_2$ and the activities of alkaline phosphatase were compared. The results are given in FIG. 15 and the enzyme-labeled streptoavidin of the present invention was more stable (FIG. 15).

EXAMPLE 7

(1) Preparation of a biotinylated alkaline phosphatase.

Dimethyl formamide (20 µl) containing 0.128 mg of D-biotinin ε-aminocapric acid N-hydroxysuccinimide ester was added to 600 µl of a 30 mM triethanolamine buffer (pH: 7.5) (containing 1 mM $MgCl_2$ and 0.1 mM $CoCl_2$) containing 30 mM of the alkaline phosphatase of the present invention and the mixture was stirred at 25° C. for three hours followed by dialyzing to a 50 mM Tris hydrochloride buffer containing 0.1M NaCl, 1 mM $MgCl_2$, 0.1 mM $CoCl_2$ and 0.1% $NaN_3$.

Comparative Example 5

Biotinylated alkaline phosphatase was prepared from CIAP by the same method as in Example 7.

Biotinyl BSA (0–5 ng) was applied by conventional means to immobilon (Millipore) and the mixture was blocked by PBS containing 1% of casein and incubated at 30° C. for one hour with 1 µg/ml of streptoavidin. After washing the membrane, this was incubated with 0.3 U/ml of the biotinylated alkaline phosphatase of the present invention and 0.3 U/ml of biotinylated CIAP. After that, it was made to react with a 1M diethanolamine buffer (pH: 9.8) (containing 5 mM $MgCl_2$) containing a luminous substance (PPD) and a detection was conducted by sensitizing with an X-ray film. Both the enzyme-labeled substance of the present invention and the CIAP-labeled one were able to detect 50 pg of biotinylated BSA.

Then the thermal stabilities of alkaline phosphatase activity in 50 mM Tris/HCl (pH: 7.5) containing 1 mM $MgCl_2$ were compared for the biotinylated alkaline phosphatase of the present invention and for the biotinylated CIAP. The results are given in FIG. 16 and the biotinylated alkaline phosphatase of the present invention was stabler.

EXAMPLE 8

(1) Probe labeled with an alkaline phosphatase.

An oligonucleotide in which Uni-Link™ Amio Modifier (manufactured by Clone Tech) was incorporated at 5'-terminal was synthesized by a common method followed by purifying.

A disuccinimidylsuberic acid solution (10 mg/ml-DMSO) (50 µl) was added to 10 µl of 0.1M $NaHCO_3$ containing 10 nmoles of the above probe, the mixture was stirred, made to react at 25° C. for 15 minutes, subjected to a gel filtration using a column of Sephadex G and the first peak containing oligonucleotide was collected. Said peak was concentrated to 100 µl, then 40 µl of 0.1M $NaHCO_3$ containing 1.5 mg of the alkaline phosphatase of the present invention was added thereto and the mixture was made to react at 25° C. overnight.

To said mixture was added about 500 ml of 20 mM Tris/HCl (pH: 7.0) containing 1.0 mM $MgCl_2$ and a purification was conducted by means of a high performance liquid chromatography (eluting solution A: 20 mM Tris/HCl of pH 7.0 containing 1.0 mM $MgCl_2$; eluting solution B: 20 mM Tris/HCl of pH 7.0 containing 1.0 mM $MgCl_2$ and 1M NaCl) using MonoQ (made by Farmacia).

Comparative Example 6

CIAP was treated by a method mentioned in Example 8 to prepare a CIAP-labeled probe.

The enzyme-labeled probe of the present invention and the CIAP-labeled probe were treated with PBS containing 1 mM $MgCl_2$ at 70° C. for two hours and their alkaline phosphatase activities were compared. The results were, as shown in FIG. 17, that the probe labeled with the enzyme of the present invention was more stable.

What we claim is:

1. A method of detecting a ligand in a sample, comprising:
   reacting a ligand in a sample with a substance bonded with a Bacillus alkaline phosphatase, the substance having a specific affinity for said ligand, so as to produce reaction products and unreacted substances;
   separating the reaction products from the unreacted substances; and
   measuring the activity of the alkaline phosphatase bonded with the reaction products or with the unreacted substances; wherein the alkaline phosphatase has the following physical and chemical properties:
   (1) the alkaline phosphatase catalyzes the following reaction:

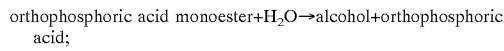
   orthophosphoric acid monoester+$H_2O$→alcohol+orthophosphoric acid;

(2) the alkaline phosphatase is used in a buffer containing a $Mg^{++}$ salt and a $Co^{++}$ salt;
   (3) the alkaline phosphatase is stable at least for 30 minutes when treated at pH 7.5 and 60° C.;
   (4) the alkaline phosphatase has a specific activity of at least 2,300 U/mg;
   (5) the alkaline phosphatase has no sugar chain; and
   (6) the alkaline phosphatase has a gel filtration molecular weight from 140,000 to 150,000 and a SDS-PAGE molecular weight from 65,000 to 67,000.

2. A method of detecting a ligand in a sample according to claim 1 in which the method of detecting a ligand in a sample is a method wherein an affinity reaction of the ligand in the sample with a substance having a specific affinity for said ligand is utilized and the activity of the alkaline phosphatase which is bonded with the substance by said reaction is measured or the activity of the alkaline phosphatase which is not bonded is measured.

3. A method of detecting a ligand in a sample according to claim 1 in which the alkaline phosphatase is bonded with a substance which has a specific affinity for the ligand.

4. A method of detecting a ligand in a sample according to claim 1 wherein the substance having a specific affinity for the ligand is bonded to a second substance and the second substance is bonded to a third substance, wherein the third substance is bonded to the alkaline phosphatase.

5. A method of detecting a ligand in a sample according to claim 1 in which the ligand is antigen, antibody, hormone, hormone receptor or nucleic acid.

6. A method of detecting a ligand in a sample according to claim 1 in which the affinity reaction of a ligand with a substance having a specific affinity for the ligand is an antigen-antibody reaction.

7. A method of detecting a ligand in a sample according to claim 1 in which the affinity reaction of a ligand with a substance having a specific affinity for the ligand is a hormone-hormone receptor reaction.

8. A method of detecting a ligand in a sample according to claim 1 in which the affinity reaction of a ligand with a substance having a specific affinity for the ligand is a nucleic acid hybridization reaction.

9. A method of detecting a ligand in a sample according to claim 1 in which any of the ligand and the substance having a specific affinity for said ligand is bonded with a solid phase.

10. A reagent for detecting a ligand in a biological sample containing a reagent for measuring an alkaline phosphatase and a ligand labeled with an alkaline phosphatase having the following physical and chemical properties or a specific bonding substance to a ligand labeled with an alkaline phosphatase having the following physical and chemical properties:

(1) the alkaline phosphatase catalyzes the following reaction:

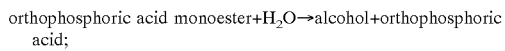

orthophosphoric acid monoester+$H_2O$→alcohol+orthophosphoric acid;

(2) the alkaline phosphatase is used in a buffer containing a $Mg^{++}$ salt and a $Co^{++}$ salt;

(3) the alkaline phosphatase is stable at least for 30 minutes when treated at pH 7.5 and 60° C.;

(4) the alkaline phosphatase has a specific activity of at least 2,300 U/mg;

(5) the alkaline phosphatase has no sugar chain; and (6) the alkaline phosphatase has a gel filtration molecular weight from 140,000 to 150,000 and a SDS-PAGE molecular weight from 65,000 to 67,000.

11. A reagent for detecting a ligand in a biological sample containing (I) a substance which has a specific affinity for a ligand to which avidin or biotin is bonded, (ii) an alkaline phosphatase having the following physical and chemical properties to which biotin or avidin is bonded and (iii) a substance for measuring an alkaline phosphatase:

(1) the alkaline phosphatase catalyzes the following reaction:

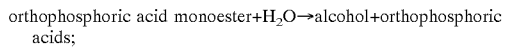

orthophosphoric acid monoester+$H_2O$→alcohol+orthophosphoric acids;

(2) the alkaline phosphatase is used in a buffer containing a $Mg^{++}$ salt and a $Co^{++}$ salt;

(3) the alkaline phosphatase is stable at least for 30 minutes when treated at pH 7.5 and 60° C.;

(4) the alkaline phosphatase has a specific activity of at least 2,300 U/mg;

(5) the alkaline phosphatase has no sugar chain; and (6) the alkaline phosphatase has a gel filtration molecular weight from 140,000 to 150,000 and a SDS-PAGE molecular weight from 65,000 to 67,000.

12. A reagent for detecting a ligand in a biological sample according to claim 10 or 11 in which the reagent for measuring the alkaline phosphatase is a 1,2-dioxetane compound or derivatives thereof, phenalenone-6-phosphate, benzophenalene-6-phosphate, 4-methylumbelliferone phosphate, p-nitrophenyl phosphate, 1-naphtholphthaleine phosphate, 5-bromo-4-chloro-3-indolyl phosphate or derivatives of those compounds.

13. A reagent for detecting a ligand in a biological sample according to claim 10 or 11 in which the ligand is antigen, antibody, hormone, hormone receptor or nucleic acid.

14. A reagent for detecting a ligand in a biological sample according to claim 10 or 11 in which the affinity reaction of a ligand with a substance having a specific affinity for the ligand is an antigen-antibody reaction.

15. A reagent for detecting a ligand in a biological sample according to claim 10 or 11 in which the affinity reaction of a ligand with a substance having a specific affinity for the ligand is a hormone-hormone receptor reaction.

16. A reagent for detecting a ligand in a biological sample according to claim 10 or 11 in which the affinity reaction of a ligand with a substance having a specific affinity for the ligand is a nucleic acid hybridization reaction.

17. A reagent for detecting a ligand in a biological sample according to claim 10 or 11 in which any of the ligand and the substance having a specific affinity for the ligand is bonded with a solid phase.

18. The method according to claim 4 wherein the second substance is a biotin and the third substance is an avidin or wherein the second substance is an avidin and the third substance is an biotin.

19. The method according to claim 18 wherein a reaction binding the avidin with the biotin occurs simultaneous with or after the step of reacting the ligand in the sample with the substance having an affinity for the ligand.

* * * * *

UNITED STATES PATENT AND TRADEMARK OFFICE
CERTIFICATE OF CORRECTION

PATENT NO. : 5,821,061
DATED : October 13, 1998
INVENTOR(S) : Shizuo Hattori, et. al.

It is certified that error appears in the above-identified patent and that said Letters Patent is hereby corrected as shown below:

Title page, item [62], change "Jan. 16, 1996" to --Jan. 12, 1996--.

Signed and Sealed this

Ninth Day of March, 1999

*Attest:*

Q. TODD DICKINSON

*Attesting Officer*   *Acting Commissioner of Patents and Trademarks*